US012226238B2

(12) United States Patent
Burnes et al.

(10) Patent No.: US 12,226,238 B2
(45) Date of Patent: *Feb. 18, 2025

(54) DETERMINING A RISK OR OCCURRENCE OF HEALTH EVENT RESPONSIVE TO DETERMINATION OF PATIENT PARAMETERS

(71) Applicant: Medtronic, Inc., Minneapolis, MN (US)

(72) Inventors: John E. Burnes, Blaine, MN (US); Mirko de Melis, Maastricht (NL); Stacy D. Beske Radford, Maple Plain, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/446,713

(22) Filed: Aug. 9, 2023

(65) Prior Publication Data

US 2023/0380773 A1    Nov. 30, 2023

Related U.S. Application Data

(63) Continuation of application No. 17/937,127, filed on Sep. 30, 2022, now Pat. No. 11,737,713, which is a
(Continued)

(51) Int. Cl.
*A61B 5/00*     (2006.01)
*A61B 5/0205*  (2006.01)
(Continued)

(52) U.S. Cl.
CPC .......... *A61B 5/7275* (2013.01); *A61B 5/0205* (2013.01); *A61B 5/1117* (2013.01);
(Continued)

(58) Field of Classification Search
None
See application file for complete search history.

(56) References Cited

U.S. PATENT DOCUMENTS 2,009,393 A    7/1935   Gioacchino
4,374,382 A    2/1983   Markowitz
(Continued)

FOREIGN PATENT DOCUMENTS

CN    1031481 A    3/1989
CN    2621634 Y    6/2004
(Continued)

OTHER PUBLICATIONS

"Guideline for the Prevention of Falls in Older Persons—American Geriatrics Society, British Geriatrics Society, and American Academy of Orthopaedic Surgeons Panel on Falls Prevention," Journal of the American Geriatrics Society, vol. 49, No. 5, May 2001, 9 pp.
(Continued)

*Primary Examiner* — Shirley X Jian
(74) *Attorney, Agent, or Firm* — Shumaker & Sieffert, P.A.

(57) ABSTRACT

This disclosure is directed to devices, systems, and techniques for monitoring a patient condition. In some examples, a medical device system includes a medical device comprising a set of sensors. Additionally, the medical device system includes processing circuitry configured to identify, based on at least one signal of the set of signals, a time of an event corresponding to the patient and set a time window based on the time of the event. Additionally, the processing circuitry is configured to save, to a fall risk database in a memory, a set of data including one or more signals of the set of signals so that the fall risk database may be analyzed
(Continued)

in order to determine a fall risk score corresponding to the patient, wherein the set of data corresponds to the time window.

20 Claims, 9 Drawing Sheets

Related U.S. Application Data continuation of application No. 16/940,817, filed on Jul. 28, 2020, now Pat. No. 11,602,313.

(51) Int. Cl.
*A61B 5/11* (2006.01)
*A61B 5/021* (2006.01)
*A61B 5/07* (2006.01)
*A61B 5/287* (2021.01)
*A61B 5/361* (2021.01)

(52) U.S. Cl.
CPC ........ *A61B 5/7264* (2013.01); *A61B 5/02125* (2013.01); *A61B 5/076* (2013.01); *A61B 5/287* (2021.01); *A61B 5/361* (2021.01); *A61B 5/686* (2013.01)

(56) References Cited

U.S. PATENT DOCUMENTS

| | | | |
|---|---|---|---|
| 4,823,797 | A | 4/1989 | Heinze et al. |
| 4,915,686 | A | 4/1990 | Frederick |
| 5,107,833 | A | 4/1992 | Barsness |
| 5,117,824 | A | 6/1992 | Keimel et al. |
| 5,127,404 | A | 7/1992 | Wyborny et al. |
| 5,168,871 | A | 12/1992 | Grevious |
| 5,271,395 | A | 12/1993 | Wahlstrand et al. |
| 5,292,343 | A | 3/1994 | Blanchette et al. |
| 5,304,119 | A | 4/1994 | Balaban et al. |
| 5,314,450 | A | 5/1994 | Thompson |
| 5,324,315 | A | 6/1994 | Grevious |
| 5,354,319 | A | 10/1994 | Wyborny et al. |
| 5,383,909 | A | 1/1995 | Keimel |
| 5,484,403 | A | 1/1996 | Yoakum et al. |
| 5,545,186 | A | 8/1996 | Olson et al. |
| 5,755,736 | A | 5/1998 | Gillberg et al. |
| 5,772,671 | A | 6/1998 | Harmon |
| 5,836,975 | A | 11/1998 | DeGroot |
| 5,842,999 | A | 12/1998 | Pruitt et al. |
| 5,876,353 | A | 3/1999 | Riff |
| 5,913,879 | A | 6/1999 | Ferek-Petric et al. |
| 5,954,670 | A | 9/1999 | Baker |
| 5,957,861 | A | 9/1999 | Combs et al. |
| 5,987,352 | A | 11/1999 | Klein et al. |
| 6,045,513 | A | 4/2000 | Stone et al. |
| 6,102,874 | A | 8/2000 | Stone et al. |
| 6,104,949 | A | 8/2000 | Pitts Crick et al. |
| 6,148,233 | A | 11/2000 | Owen et al. |
| 6,154,674 | A | 11/2000 | Meier |
| 6,221,011 | B1 | 4/2001 | Bardy |
| 6,230,059 | B1 | 5/2001 | Duffin |
| 6,263,243 | B1 | 7/2001 | Lang |
| 6,277,072 | B1 | 8/2001 | Bardy |
| 6,280,380 | B1 | 8/2001 | Bardy |
| 6,280,409 | B1 | 8/2001 | Stone et al. |
| 6,336,903 | B1 | 1/2002 | Bardy |
| 6,405,085 | B1 | 6/2002 | Graupner et al. |
| 6,412,490 | B1 | 7/2002 | Lee |
| 6,449,509 | B1 | 9/2002 | Park et al. |
| 6,459,929 | B1 | 10/2002 | Hopper et al. |
| 6,463,326 | B1 | 10/2002 | Hartley et al. |
| 6,473,640 | B1 | 10/2002 | Erlebacher |
| 6,480,733 | B1 | 11/2002 | Turcott |
| 6,512,940 | B1 | 1/2003 | Brabec et al. |
| 6,512,949 | B1 | 1/2003 | Combs et al. |
| 6,522,915 | B1 | 2/2003 | Ceballos et al. |
| 6,572,557 | B2 | 6/2003 | Tchou et al. |
| 6,595,927 | B2 | 7/2003 | Pitts-Crick et al. |
| 6,620,467 | B2 | 9/2003 | Sudo et al. |
| 6,622,046 | B2 | 9/2003 | Fraley et al. |
| 6,625,493 | B2 | 9/2003 | Kroll et al. |
| 6,647,295 | B2 | 11/2003 | Florio et al. |
| 6,671,549 | B2 | 12/2003 | Van Dam et al. |
| 6,719,701 | B2 | 4/2004 | Lade |
| 6,788,970 | B1 | 9/2004 | Park et al. |
| 6,821,249 | B2 | 11/2004 | Casscells, III et al. |
| 6,866,629 | B2 | 3/2005 | Bardy |
| 6,892,094 | B2 | 5/2005 | Ousdigian et al. |
| 6,895,275 | B2 | 5/2005 | Markowitz et al. |
| 6,907,288 | B2 | 6/2005 | Daum |
| 6,931,272 | B2 | 8/2005 | Burnes |
| 6,945,934 | B2 | 9/2005 | Bardy |
| 6,960,167 | B2 | 11/2005 | Bardy |
| 7,035,684 | B2 | 4/2006 | Lee |
| 7,127,290 | B2 | 10/2006 | Girouard et al. |
| 7,141,026 | B2 | 11/2006 | Aminian et al. |
| 7,149,584 | B1 | 12/2006 | Koh et al. |
| 7,177,681 | B2 | 2/2007 | Zhu |
| 7,177,684 | B1 | 2/2007 | Kroll et al. |
| 7,184,821 | B2 | 2/2007 | Belalcazar et al. |
| 7,248,916 | B2 | 7/2007 | Bardy |
| 7,272,442 | B2 | 9/2007 | Freeberg |
| 7,308,309 | B1 | 12/2007 | Koh |
| 7,310,551 | B1 | 12/2007 | Koh et al. |
| 7,313,434 | B2 | 12/2007 | Belalcazar et al. |
| 7,340,296 | B2 | 3/2008 | Stahmann et al. |
| 7,387,610 | B2 | 6/2008 | Stahmann et al. |
| 7,389,143 | B2 | 6/2008 | Hopper et al. |
| 7,541,934 | B2 | 6/2009 | Fredriksson et al. |
| 7,647,106 | B2 | 1/2010 | Virag et al. |
| 7,937,135 | B2 | 5/2011 | Ghanem et al. |
| 7,991,471 | B2 | 8/2011 | Ghanem et al. |
| 7,996,087 | B2 | 8/2011 | Cowan et al. |
| 8,206,325 | B1 | 6/2012 | Najafi et al. |
| 8,255,046 | B2 | 8/2012 | Sarkar et al. |
| 8,428,720 | B2 | 4/2013 | Corbucci et al. |
| 8,491,504 | B2 | 7/2013 | Hirth |
| 8,736,453 | B2 | 1/2014 | Wilson et al. |
| 8,688,201 | B2 | 4/2014 | Corbucci et al. |
| 8,744,572 | B1 | 6/2014 | Greenhut et al. |
| 8,818,505 | B2 | 8/2014 | Bhunia et al. |
| 8,845,557 | B1 | 9/2014 | Giuffrida et al. |
| 8,888,745 | B2 | 11/2014 | Van Der Graaf et al. |
| 8,990,041 | B2 | 3/2015 | Grabiner et al. |
| 9,005,141 | B1 | 4/2015 | Najafi et al. |
| 9,318,012 | B2 | 4/2016 | Johnson et al. |
| 9,332,924 | B2 | 5/2016 | Thakur et al. |
| 9,403,000 | B2 | 8/2016 | Lyons et al. |
| 9,452,101 | B2 | 9/2016 | Tomlinson et al. |
| 9,795,322 | B1 | 10/2017 | Karunaratne et al. |
| 9,848,778 | B2 | 12/2017 | Soykan et al. |
| 9,901,290 | B2 | 2/2018 | Najafi et al. |
| 9,907,959 | B2 | 3/2018 | Skelton |
| 10,052,062 | B2 | 8/2018 | De Sapio et al. |
| 10,070,824 | B2 | 9/2018 | LeLorier |
| 10,124,172 | B2 | 11/2018 | Lyons et al. |
| 10,143,395 | B2 | 12/2018 | Chakravarthy |
| 10,166,001 | B2 | 1/2019 | An et al. |
| 10,182,729 | B2 | 1/2019 | Zielinski et al. |
| 10,226,631 | B2 | 3/2019 | Kane |
| 10,264,997 | B1 | 4/2019 | Romrell et al. |
| 10,335,047 | B2 | 7/2019 | Gunderson |
| 10,506,933 | B2 | 12/2019 | Soykan et al. |
| 10,610,132 | B2 | 4/2020 | Gunderson et al. |
| 10,765,359 | B2 | 9/2020 | Cho et al. |
| 11,375,905 | B2 | 7/2022 | Gunderson et al. |
| 11,602,313 | B2 | 3/2023 | Burnes et al. |
| 11,717,186 | B2 | 8/2023 | Gunderson |
| 2001/0004234 | A1 | 6/2001 | Petelenz et al. |
| 2001/0011153 | A1 | 8/2001 | Bardy |
| 2001/0021801 | A1 | 9/2001 | Bardy |
| 2001/0039504 | A1 | 11/2001 | Lindberg et al. |
| 2002/0004672 | A1 | 1/2002 | Florio et al. |
| 2002/0026104 | A1 | 2/2002 | Bardy |

(56) References Cited

U.S. PATENT DOCUMENTS

| | | |
|---|---|---|
| 2002/0115939 A1 | 8/2002 | Mulligan et al. |
| 2002/0132044 A1 | 9/2002 | Quarles |
| 2003/0028221 A1 | 2/2003 | Zhu et al. |
| 2003/0055461 A1 | 3/2003 | Girouard et al. |
| 2003/0125611 A1 | 7/2003 | Bardy |
| 2003/0149367 A1 | 8/2003 | Kroll et al. |
| 2003/0212445 A1 | 11/2003 | Weinberg |
| 2003/0220580 A1 | 11/2003 | Alt |
| 2004/0015197 A1 | 1/2004 | Gunderson |
| 2004/0082969 A1 | 4/2004 | Kerr |
| 2004/0102712 A1 | 5/2004 | Belalcazar et al. |
| 2004/0112151 A1 | 6/2004 | Maxwell et al. |
| 2004/0122484 A1 | 6/2004 | Hatlestad et al. |
| 2004/0172080 A1 | 9/2004 | Stadler et al. |
| 2004/0193154 A1 | 9/2004 | Leatherbury et al. |
| 2004/0249388 A1 | 12/2004 | Michelson |
| 2005/0090852 A1 | 4/2005 | Layne et al. |
| 2005/0096645 A1 | 5/2005 | Wellman et al. |
| 2005/0107768 A1 | 5/2005 | Ting |
| 2005/0115561 A1 | 6/2005 | Stahmann et al. |
| 2005/0124908 A1 | 6/2005 | Belalcazar et al. |
| 2006/0020295 A1 | 1/2006 | Brockway et al. |
| 2006/0030892 A1 | 2/2006 | Kadhiresan et al. |
| 2006/0074434 A1 | 4/2006 | Wenstrom et al. |
| 2006/0097331 A1 | 5/2006 | Hattori et al. |
| 2006/0106415 A1 | 5/2006 | Gabbay |
| 2006/0174898 A1 | 8/2006 | Brown |
| 2006/0241701 A1 | 10/2006 | Markowitz et al. |
| 2006/0276848 A1 | 12/2006 | Min et al. |
| 2006/0293609 A1 | 12/2006 | Stahmann et al. |
| 2007/0010738 A1 | 1/2007 | Mark et al. |
| 2007/0021678 A1 | 1/2007 | Beck et al. |
| 2007/0067005 A1 | 3/2007 | Schatz et al. |
| 2007/0088394 A1 | 4/2007 | Jacobson |
| 2007/0088397 A1 | 4/2007 | Jacobson |
| 2007/0142732 A1 | 6/2007 | Brockway et al. |
| 2007/0156061 A1 | 7/2007 | Hess |
| 2007/0179515 A1 | 8/2007 | Matsutani et al. |
| 2007/0249992 A1 | 10/2007 | Bardy |
| 2008/0024293 A1 | 1/2008 | Stylos |
| 2008/0027349 A1 | 1/2008 | Stylos |
| 2008/0082001 A1 | 4/2008 | Hatlestad et al. |
| 2008/0154298 A1 | 6/2008 | Grayzel et al. |
| 2008/0161657 A1 | 7/2008 | Bullens et al. |
| 2008/0255626 A1 | 10/2008 | Fricke et al. |
| 2008/0281550 A1 | 11/2008 | Hogle et al. |
| 2008/0288200 A1 | 11/2008 | Noble |
| 2009/0030426 A1 | 1/2009 | Zinn et al. |
| 2009/0036917 A1 | 2/2009 | Anderson |
| 2009/0137946 A1 | 5/2009 | Nassiri et al. |
| 2009/0221937 A1 | 9/2009 | Smith et al. |
| 2009/0278934 A1 | 11/2009 | Ecker et al. |
| 2009/0312649 A1 | 12/2009 | Lian et al. |
| 2010/0010361 A1 | 1/2010 | Boute et al. |
| 2010/0030090 A1 | 2/2010 | Zhang et al. |
| 2010/0030227 A1 | 2/2010 | Kast et al. |
| 2010/0030292 A1 | 2/2010 | Sarkar et al. |
| 2010/0030293 A1 | 2/2010 | Sarkar et al. |
| 2010/0087745 A1 | 4/2010 | Fischell et al. |
| 2010/0094252 A1 | 4/2010 | Wengreen et al. |
| 2010/0011424 A1 | 5/2010 | Donofrio et al. |
| 2010/0114241 A1 | 5/2010 | Donofrio et al. |
| 2010/0198097 A1 | 8/2010 | Sowelam |
| 2010/0198140 A1 | 8/2010 | Lawson |
| 2010/0210975 A1 | 8/2010 | Anthony, III et al. |
| 2010/0228308 A1 | 9/2010 | Cowan et al. |
| 2010/0331868 A1 | 12/2010 | Bardy |
| 2011/0040572 A1 | 2/2011 | Chmiel et al. |
| 2011/0071586 A1 | 3/2011 | Jacobson |
| 2011/0077865 A1 | 3/2011 | Chen et al. |
| 2011/0082350 A1 | 4/2011 | Koh |
| 2011/0106201 A1 | 5/2011 | Bhunia |
| 2011/0148400 A1 | 6/2011 | Doerr et al. |
| 2011/0172545 A1 | 7/2011 | Grudic et al. |
| 2011/0190835 A1 | 8/2011 | Brockway et al. |
| 2011/0288379 A1 | 11/2011 | Wu |
| 2012/0083705 A1 | 4/2012 | Yuen et al. |
| 2012/0109235 A1 | 5/2012 | Jacobson |
| 2012/0109236 A1 | 5/2012 | Jacobson et al. |
| 2012/0109237 A1 | 5/2012 | Xiao et al. |
| 2012/0157874 A1 | 6/2012 | Thakur et al. |
| 2012/0259577 A1 | 10/2012 | Ganyi |
| 2012/0271177 A1 | 10/2012 | Emerson et al. |
| 2012/0277546 A1 | 11/2012 | Soykan et al. |
| 2012/0283705 A1 | 11/2012 | Lee et al. |
| 2013/0079861 A1 | 3/2013 | Reinert et al. |
| 2013/0085677 A1 | 4/2013 | Modi et al. |
| 2013/0123684 A1 | 5/2013 | Giuffrida et al. |
| 2013/0066169 A1 | 9/2013 | Rys et al. |
| 2013/0304414 A1 | 11/2013 | Levy et al. |
| 2014/0022079 A1 | 1/2014 | Wilson et al. |
| 2014/0024971 A1 | 1/2014 | Bunn et al. |
| 2014/0088442 A1 | 3/2014 | Soykan et al. |
| 2014/0128778 A1 | 5/2014 | Chan et al. |
| 2014/0128963 A1 | 5/2014 | Quill et al. |
| 2014/0276130 A1 | 9/2014 | Mirelman et al. |
| 2014/0276928 A1 | 9/2014 | Venderpool et al. |
| 2014/0330172 A1 | 11/2014 | Jovanov et al. |
| 2014/0358193 A1 | 12/2014 | Lyons et al. |
| 2014/0364769 A1 | 12/2014 | Chang et al. |
| 2015/0011840 A1 | 1/2015 | Gavriely |
| 2015/0185044 A1 | 7/2015 | Nie et al. |
| 2015/0257654 A1 | 9/2015 | Bennett-Guerrero |
| 2015/0286285 A1 | 10/2015 | Pantelopoulos et al. |
| 2015/0302720 A1 | 10/2015 | Zhang et al. |
| 2015/0313552 A1 | 11/2015 | Zhang et al. |
| 2015/0342540 A1 | 12/2015 | An et al. |
| 2016/0038093 A1 | 2/2016 | Sharma et al. |
| 2016/0045140 A1 | 2/2016 | Kitamura et al. |
| 2016/0058333 A1 | 3/2016 | Arnold et al. |
| 2016/0100776 A1 | 4/2016 | Najafi et al. |
| 2016/0155313 A1 | 6/2016 | Chang et al. |
| 2016/0175007 A1 | 6/2016 | Valbuena et al. |
| 2016/0192890 A1 | 7/2016 | Averina et al. |
| 2016/0209232 A1 | 7/2016 | Yang et al. |
| 2016/0220153 A1 | 8/2016 | Annegarn et al. |
| 2016/0256694 A1 | 9/2016 | Shuros |
| 2017/0056667 A1 | 3/2017 | Kane |
| 2017/0067933 A1 | 3/2017 | Miller et al. |
| 2017/0112463 A1 | 4/2017 | An et al. |
| 2017/0155877 A1 | 6/2017 | Johnson et al. |
| 2017/0188897 A1 | 7/2017 | Thein et al. |
| 2017/0213145 A1 | 7/2017 | Pathak et al. |
| 2017/0258346 A1 | 9/2017 | Vanderpool et al. |
| 2017/0344919 A1 | 11/2017 | Chang et al. |
| 2018/0035898 A1 | 2/2018 | Gunderson |
| 2018/0035920 A1 | 2/2018 | Gunderson et al. |
| 2018/0035924 A1 | 2/2018 | Gunderson et al. |
| 2018/0035956 A1 | 2/2018 | Gunderson et al. |
| 2018/0055386 A1 | 3/2018 | Zielinski et al. |
| 2018/0070889 A1 | 3/2018 | Lee et al. |
| 2018/0085021 A1 | 3/2018 | Chakravarthy |
| 2018/0103874 A1 | 4/2018 | Lee et al. |
| 2018/0132793 A1 | 5/2018 | Katra |
| 2018/0168460 A1 | 6/2018 | Morris |
| 2018/0168502 A1 | 6/2018 | Cho et al. |
| 2018/0177436 A1 | 6/2018 | Chang et al. |
| 2018/0333083 A1 | 11/2018 | Orellano |
| 2019/0069794 A1 | 3/2019 | Bardy et al. |
| 2019/0069851 A1 | 3/2019 | Sharma et al. |
| 2019/0103007 A1 | 4/2019 | Tan et al. |
| 2019/0150852 A1 | 5/2019 | Stone et al. |
| 2019/0167205 A1 | 6/2019 | An et al. |
| 2019/0214146 A1 | 7/2019 | Dunias et al. |
| 2020/0046982 A1 | 2/2020 | Min et al. |
| 2020/0174517 A1 | 6/2020 | Martinez et al. |
| 2020/0187864 A1 | 6/2020 | Sharma |
| 2020/0297230 A1 | 9/2020 | Thakur et al. |
| 2021/0059568 A1 | 3/2021 | Gunderson |
| 2021/0093253 A1 | 4/2021 | Sarkar et al. |
| 2021/0153751 A1 | 5/2021 | Gunderson et al. |
| 2021/0345891 A1 | 11/2021 | Gill et al. |
| 2022/0000421 A1 | 1/2022 | Ippolito |

(56) References Cited

U.S. PATENT DOCUMENTS

| | | |
|---|---|---|
| 2022/0031253 A1 | 2/2022 | Burnes et al. |
| 2022/0273236 A1 | 5/2022 | Zhou |
| 2023/0021724 A1 | 1/2023 | Burnes et al. |

FOREIGN PATENT DOCUMENTS

| | | |
|---|---|---|
| CN | 2702718 Y | 6/2005 |
| CN | 202342097 U | 7/2012 |
| DE | 469951 C | 1/1929 |
| DE | 4243641 A1 | 9/1994 |
| DE | 10148440 A1 | 4/2003 |
| EP | 1997427 A1 | 3/2008 |
| EP | 3034128 A1 | 6/2016 |
| JP | 2001502937 A | 3/2001 |
| JP | 2007516031 A | 6/2007 |
| JP | 2008528084 A | 7/2008 |
| JP | 2011092065 A | 5/2011 |
| WO | 9813091 A1 | 4/1998 |
| WO | 9833554 A1 | 8/1998 |
| WO | 200064336 A1 | 11/2000 |
| WO | 2001032260 A1 | 5/2001 |
| WO | 2002067449 A2 | 8/2002 |
| WO | 2003061759 A1 | 7/2003 |
| WO | 2004093985 A1 | 11/2004 |
| WO | 2005044116 A1 | 5/2005 |
| WO | 2005060306 A1 | 6/2005 |
| WO | 2006070124 A1 | 7/2006 |
| WO | 2006081432 A1 | 8/2006 |
| WO | 2007033194 A2 | 3/2007 |
| WO | 2007079354 A2 | 7/2007 |
| WO | 2008016551 A1 | 2/2008 |
| WO | 2010030942 A1 | 3/2010 |
| WO | 2012098356 A1 | 7/2012 |
| WO | 2014083538 A1 | 6/2014 |
| WO | 2017142488 A1 | 8/2017 |
| WO | 2020002566 A1 | 1/2020 |

OTHER PUBLICATIONS

Adamson et al, "Continuous Autonomic Assessment in Patients with Symptomatic Heart Failure . . . " Circulation Journal of American Heart Association, vol. 110, No. 16, Jun. 30, 2004, pp. 2389-2394.

Alberts et al., "Using Accelerometer and Gyroscopic Measures to Quantify Postural Stability," Journal of Athletic Training, vol. 50, No. 6, Jun. 2015, 11 pp.

Baer, et al. "Electronic Home Monitoring of Congestive Heart Failure Patients: Design and Feasibility", Congestive Heart Failure, vol. 5, May/Jun. 1999, pp. 105-113.

Barde et al., "What to use to express the variability of data: Standard deviation or standard error of mean?," Perspectives In clinical Research, vol. 3, No. 3, Jul. 2012, 4 pp.

Berman et al. "Transthoracic Electrical Impedance as a Guide to Intravascular Overload", Archives Surgery, vol. 102, Jan. 1971, pp. 61-64.

Chang et al., "A Wireless Accelerometer-Based Body Posture Stability Detection System and Its Application for Meditation Practitioners," Sensors, ISSN: 1424-8220, Dec. 18, 2012, 13 pp.

Clark et al., "Improving the Validity of Activity of Daily Living Dependency Risk Assessment," Journal of Applied Gerontology: The Official Journal of the Southern Gerontological Society, vol. 34, No. 3, Apr. 2015, 14 pp.

Corrected Notice of Allowance from U.S. Appl. No. 16/940,817 dated Feb. 7, 2023, 2 pp.

Devries et al., "Outcome instruments to measure frailty: A systematic review," Ageing Research Reviews, vol. 10, accepted Sep. 2010, published Jan. 2011, 11 pp.

Ganea et al., "Multi-Parametric Evaluation of Sit-to-Stand and Stand-to-Sit Transitions in Elderly People," Medical Engineering and Physics, vol. 33. No. 9, Apr. 23, 2011, pp. 1086-1093.

Giuberti et al., "Automatic UPDRS Evaluation in the Sit-to-Stand Task of Parkinsonians: Kinetic Analysis and Comparative Outlook on the Leg Agility Task", IEEE Journal of Biomedical and Health Informatics, vol. 19, No. 3, May 2015, pp. 2168-2194.

Hubble et al., "Wearable Sensor Use for Assessing Standing Balance and Walking Stability in People with Parkinson's Disease: A Systematic Review," Plos One, Apr. 20, 2015, 22 pp.

International Search Report and Written Opinion of International Application No. PCT/US2021/041742, dated Nov. 4, 2021, 13 pp.

Kearns et al., "Path Tortuosity in Everyday Movements of Elderly Persons Increases Fall Prediction Beyond Knowledge of Fall History, Medication Use and Standardized Gait and Balance Assessments," Journal of the American Medical Directors Association, (JAMDA), vol. 13, No. 7, Sep. 2012, 7 pp.

Kearns et al., "Tortuosity in Movement Paths Is Related to Cognitive Impairment—Wireless Fractal Estimation in Assisted Living Facility Residents," Methods of Information in Medicine, vol. 49, No. 6, Mar. 2010, 7 pp.

Kearns et al., "Wireless telesurveillance system for detecting dementia," Gerontechnology, vol. 10, No. 2, Jan. 2011, 13 pp.

Lusignan, et al. "Compliance and Effectiveness of 1 Year's Home Telemonitoring, The Report of a Pilot Study . . . " European Journal of Heart Failure, vol. 3, Apr. 2001, pp. 723-730.

McCrory et al., "Speed of Heart Rate Recovery in Response to Orthostatic Challenge—A Strong Risk Marker of Mortality," Circulation Research, vol. 119, No. 5, Aug. 2016, 10 pp.

Millor et al., "Kinematic Parameters to Evaluate Functional Performance of Sit-to-Stand and Stand-to-Sit Transitions Using Motion Sensor Devices: a Systematic Review," IEEE Transactions on Neural Systems and Rehabilitation Engineering, vol. 22, No. 5, Jun. 2014, 11 pp.

Notice of Allowance from U.S. Appl. No. 16/940,817 dated Jan. 31, 2023, 10 pp.

Odden et al., "Rethinking the Association of High Blood Pressure With Mortality in Elderly Adults: The Impact of Frailty," Archives of Internal Medicine, vol. 172, No. 15, Aug. 2012, 7 pp.

Prosecution History from U.S. Appl. No. 16/940,817, dated Jun. 22, 2022 through Sep. 22, 2022, 31 pp.

Prosecution History from U.S. Appl. No. 17/937,127, dated Dec. 14, 2022 through Jun. 7, 2023, 68 pp.

Rigoberto et al., "Postural sway parameters using a triaxial accelerometer: Comparing elderly and young healthy adults," Computer Methods in Biomechanics and Biomedical Engineering, Feb. 21, 2011, 12 pp.

Robertson et al., "Frailty and Cognitive impairment—A review of the evidence and causal mechanisms," Ageing Research Reviews, vol. 12, No. 4, Sep. 2013, 12 pp.

Romero-Ortuno et al., "A Frailty Instrument for primary care: findings from the Survey of Health, Ageing and Retirement in Europe (Share)," BMC Geriatrics, vol. 10, No. 57, Aug. 2010, 12 pp.

U.S. Appl. No. 18/339,719, filed Jun. 22, 2023, naming inventors Gunderson.

Veltink, et al., "Detection of Static and Dynamic Activities Using Uniaxial Accelerometers", IEEE Transactions on Rehabilitation Engineering, vol. 4, No. 4, Dec. 1996, 11 pp.

Wieling et al., "Testing for Autonomic Neuropathy: Heart Rate Changes After Orthostatic Manoeuvers and Static Muscle Contractions," Clinical Science(London), vol. 64, No. 6, Jun. 1, 1983, pp. 581-586.

Wuerz et al., "Effects of Prehospital Medications on Mortality and Length of Stay in Congestive Heart Failure", Annals of Emergency Medicine, vol. 21, No. 6, Jun. 1992, pp. 669-674.

Communication pursuant to Article 94(3) EPC from counterpart European Application No. 21752358.8 dated Nov. 13, 2024, 7 pp.

DETERMINING A RISK OR OCCURRENCE OF HEALTH EVENT RESPONSIVE TO DETERMINATION OF PATIENT PARAMETERS

This application is a continuation of U.S. patent application Ser. No. 17/937,127, filed 30 Sep. 2022, which is a continuation of U.S. patent application Ser. No. 16/940,817, filed 28 Jul. 2020, the entire content of each of which is incorporated herein by reference.

TECHNICAL FIELD

The disclosure relates generally to medical device systems and, more particularly, medical device systems configured to monitor patient parameters.

BACKGROUND

Some types of medical devices may be used to monitor one or more physiological parameters of a patient. Such medical devices may include, or may be part of a system that includes, sensors that detect signals associated with such physiological parameters. Values determined based on such signals may be used to assist in detecting changes in patient conditions, in evaluating the efficacy of a therapy, or in generally evaluating patient health.

SUMMARY

In general, the disclosure is directed to devices, systems, and techniques for monitoring a fall risk of a patient. The fall risk, in some cases, may indicate a likelihood that the patient will fall within a period of time following a reference time. As used herein, the term "fall" refers to an involuntary body position change induced by gravity, such as a fall from a standing position or a fall from a sitting position. A medical device system may determine a fall risk corresponding to a patient by monitoring one or more patient parameters over a period of time and analyzing a response of the one or more patient parameters to certain events. For example, the medical device system may determine how the one or more patient parameters change in response to a body position change (e.g., a sit-to-stand movement) or in response to a cardiac event (e.g., a premature ventricular contraction (PVC)) and determine the fall risk of the patient based on the determined change.

An implantable medical device (IMD) may include one or more electrodes configured to measure an electrogram (EGM) of the patient. The EGM may, in some cases, indicate a ventricular depolarization (e.g., an R-wave) of the patient's heart and a heart rate of the patient. Additionally, the IMD may determine tissue perfusion based on impedance sensed via the electrodes, and/or oxygen saturation using an optical sensor. Processing circuitry may determine a pulse transit time (PTT) associated with the patient based on the EGM, the impedance, the measured oxygen saturation, or any combination thereof. PTT is correlated with blood pressure. As such, processing circuitry may be configured to use a PTT measurement performed by the IMD as a representation of the blood pressure of the patient. In this way, the processing circuitry may be configured to track the blood pressure and the heart rate of the patient over a period of time.

Additionally, the IMD may include a 3-axis accelerometer which generates an accelerometer signal indicative of a posture of the patient, an activity level of the patient, a gait of the patient, and a body angle of the patient, as examples. This accelerometer signal may be used by the processing circuitry to perform a fall risk analysis. For example, the processing circuitry may be configured to identify one or more body position changes and determine how one or more patient parameters change in response to the each body position change of the one or more body position changes. For example, it may be expected that a heart rate and a blood pressure of the patient increases responsive to a sit-to-stand movement performed by the patient. Processing circuitry may determine that the patient is at an increased risk of falling if the blood pressure increase and the heart rate increase following a sit-to-stand movement of the patient are less than the expected increases. Additionally, or alternatively, the processing circuitry may determine that the patient is at an increased risk of falling in response to a change in a gait of the patient over time, a change in a stand-up speed of the patient over time, or any other determinable change in a patient parameter over time.

The techniques of this disclosure may provide one or more advantages. For example, it may be beneficial to create one or more "bins" for evaluating data collected by the IMD in order to determine a fall risk of the patient, such as a sit-to-stand bin, a lying-to-sit bin, and a lying-to-stand bin. Processing circuitry may analyze the heart rate and the blood pressure (and/or other parameters) following each sit-to-stand movement in the sit-to-stand bin, analyze the heart rate and the blood pressure following each lying-to-sit movement in the lying-to-sit bin, and analyze each lying-to-stand movement in the lying-to-stand bin. Based on analysis of each bin, e.g., based on a significant parameter value change over time in one or more of the bins, the processing circuitry may determine a fall risk of the patient. Segregating the data into different bins for different movements or events may facilitate a more meaningful comparison of the response of the patient to the events over time and more accurate identification of the risk of falling.

In some examples, a medical device system includes a medical device comprising a set of sensors configured to sense a set of signals, wherein the set of sensors comprises a motion sensor configured to generate a motion sensor signal which indicates a motion of a patient, wherein the set of signals includes the motion sensor signal. Additionally, a medical device system includes processing circuitry configured to identify, based on at least one signal of the set of signals, a time of an event corresponding to the patient, set a time window based on the time of the event, and save, to a fall risk database in a memory, a set of data including one or more signals of the set of signals so that the fall risk database may be analyzed in order to determine a fall risk score corresponding to the patient, wherein the set of data corresponds to the time window.

In some examples, a method includes sensing, by a medical device comprising a set of sensors, a set of signals, wherein the set of sensors comprises a motion sensor configured to generate a motion sensor signal which indicates a motion of a patient, wherein the set of signals includes the motion sensor signal, identifying, by the processing circuitry based on at least one signal of the set of signals, a time of an event corresponding to the patient and setting, by the processing circuitry, a time window based on the time of the event. Additionally, the method includes saving, by the processing circuitry to a fall risk database in a memory, a set of data including one or more signals of the set of signals so that the fall risk database may be analyzed in order to determine a fall risk score corresponding to the patient, wherein the set of data corresponds to the time window.

In some examples, a non-transitory computer-readable medium includes instructions for causing one or more processors to sense, by a medical device comprising a set of sensors, a set of signals, wherein the set of sensors comprises a motion sensor configured to generate a motion sensor signal which indicates a motion of a patient, wherein the set of signals includes the motion sensor signal and identify, based on at least one signal of the set of signals, a time of an event corresponding to the patient. Additionally, the instructions cause the one or more processors to set a time window based on the time of the event; and save, to a fall risk database in a memory, a set of data including one or more signals of the set of signals so that the fall risk database may be analyzed in order to determine a fall risk score corresponding to the patient, where the set of data corresponds to the time window.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

DETAILED DESCRIPTION

This disclosure describes techniques for monitoring a fall risk of a patient. For example, an implantable medical device (IMD) may measure a set of patient parameters over a period of time. Processing circuitry may identify, based on one or more signals generated by the IMD, one or more events associated with the patient such as one or more body position changes and/or one or more cardiac events. The processing circuitry may analyze a manner in which at least one patient parameter of the set of patient parameters responds to each event of the one or more events. The processing circuitry may determine, based on the response of the patient parameters to the identified body position changes, the fall risk of the patient.

Falls may represent a significant challenge to some patients. As such, it may be beneficial to monitor one or more patient parameters, such as one or more patient parameters indicated by signals collected by medical device(s), in order to determine whether a patient is at risk of falling in the future. In some cases, falls are caused by arrhythmias such as any one or combination of asystole arrhythmias, tachycardia arrhythmias, bradycardia arrhythmias, or atrial fibrillation (AF). For example, a patient with bradycardia may have an abnormally low blood pressure or abnormally low heart rate. Consequently, a patient with bradycardia may experience lightheadedness when standing up, walking, or otherwise exerting effort. This lightheadedness may cause the patient to fall, in some cases. Other diseases or conditions such as Heart Failure, chronic obstructive pulmonary disease (COPD), seizures, and dementia (e.g., Parkinson's Disease, Multiple Sclerosis, and Alzheimer's Disease), may also lead to falls. In addition, older patients may be at an increased risk of falling.

In any case, it may be beneficial to analyze signals recorded by one or more medical devices in order to track a patient's risk of falling. If a patient is determined to be at an increased risk of falling, processing circuitry may output an alert, output a recommendation for treatment, and/or cause one or more medical devices to deliver treatment to the patient. In some examples, the processing circuitry monitor and bin one or more parameters including blood pressure, heart rate, tissue perfusion, motion data, and gyroscopic data. The processing circuitry may analyze the one or more parameters in order to determine the patient's risk of falling.

Figure 1:
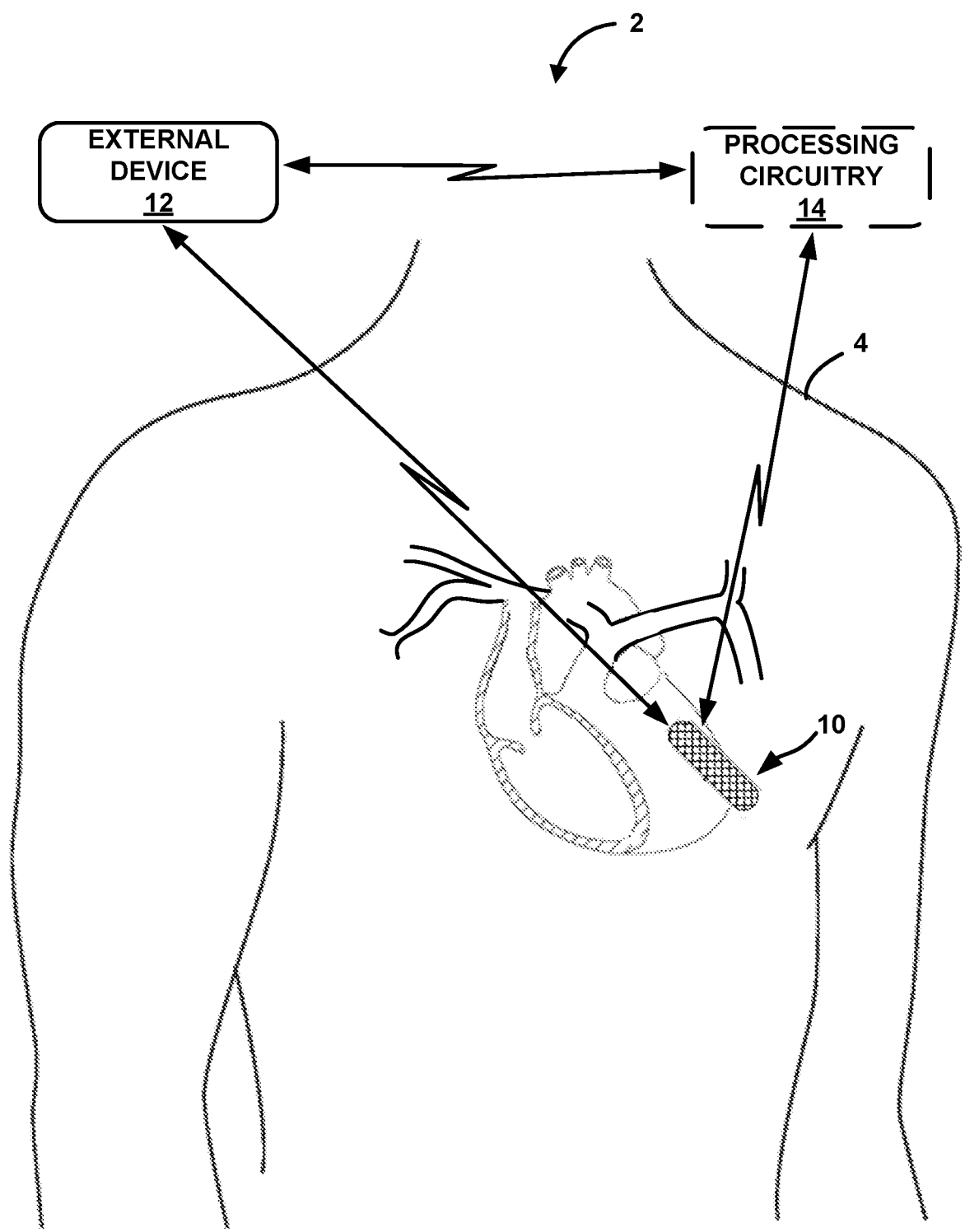
FIG. 1 is a conceptual diagram illustrating an environment of an example medical device system in conjunction with a patient, in accordance with one or more techniques of this disclosure.

FIG. 1 is a conceptual diagram illustrating an environment of an example medical device system 2 in conjunction with a patient 4, in accordance with one or more techniques of this disclosure. The example techniques may be used with an IMD 10, which may be in wireless communication with at least one of external device 12 and other devices not pictured in FIG. 1. Processing circuitry 14 is conceptually illustrated in FIG. 1 as separate from IMD 10 and external device 12 but may be processing circuitry of IMD 10 and/or processing circuitry of external device 12. In general, the techniques of this disclosure may be performed by processing circuitry 14 of one or more devices of a system, such as one or more devices that include sensors that provide signals, or processing circuitry of one or more devices that do not include sensors, but nevertheless analyze signals using the techniques described herein. For example, another external device (not pictured in FIG. 1) may include at least a portion of processing circuitry 14, the other external device configured for remote communication with IMD 10 and/or external device 12 via a network.

In some examples, IMD 10 is implanted outside of a thoracic cavity of patient 4 (e.g., subcutaneously in the pectoral location illustrated in FIG. 1). IMD 10 may be positioned near the sternum near or just below the level of patient 4's heart, e.g., at least partially within the cardiac silhouette. In some examples, IMD 10 takes the form of a LINQ™ Insertable Cardiac Monitor (ICM), available from Medtronic plc, of Dublin, Ireland.

Clinicians sometimes diagnose patients with medical conditions based on one or more observed physiological signals collected by physiological sensors, such as electrodes, optical sensors, chemical sensors, temperature sensors, acoustic sensors, and motion sensors. In some cases, clinicians apply non-invasive sensors to patients in order to sense one or more physiological signals while a patient is in a clinic for a medical appointment. However, in some examples, physiological markers (e.g., irregular heartbeats and long-term respiration trends) of a patient condition are rare or are difficult to observe over a relatively short period of time. As such, in these examples, a clinician may be unable to observe the physiological markers needed to diagnose a patient with a medical condition while monitoring one or more physiological signals of the patient during a medical appointment. Additionally, it may be beneficial to monitor one or more patient parameters for an extended period of time (e.g., days, weeks, or months) so that the one or more parameters may be analyzed to identify one or more changes or trends over the extended period of time. In the example illustrated in FIG. 1, IMD 10 is implanted within patient 4 to continuously record one or more physiological signals of patient 4 over an extended period of time.

In some examples, IMD 10 includes one or more sensor(s) which are configured to detect physiological signals of patient 4. For example, IMD 10 includes a set of electrodes (not illustrated in FIG. 1). The set of electrodes are configured to detect one or more signals associated with cardiac functions and/or lung functions of patient 4. In some examples, IMD 10 may sense an electrogram (EGM) via the set of electrodes. The EGM may represent one or more physiological electrical signals corresponding to the heart of patient 4. For example, the EGM may indicate ventricular depolarizations (R-waves), atrial depolarizations (P-waves, ventricular Repolarizations (T-waves), among other events. Information relating to the aforementioned events, such as time separating one or more of the events, may be applied for a number of purposes, such as to determine whether an arrhythmia is occurring and/or predict whether an arrhythmia is likely to occur. In some examples, the IMD 10 may be configured to detect a tissue impedance signal via the set of electrodes. The tissue impedance signal may represent a resistance value between one or more of the set of electrodes and subcutaneous tissue of patient 4. The tissue impedance may be applied for a number of purposes, such as to determine whether an arrhythmia is occurring and/or predict whether an arrhythmia is likely to occur.

Moreover, IMD 10 may additionally or alternatively include one or more optical sensors, motion sensors (e.g., accelerometers), temperature sensors, chemical sensors, pressure sensors, or any combination thereof. Such sensors may detect one or more physiological parameters indicative of a patient condition.

For example, IMD 10 includes one or more accelerometers. An accelerometer of IMD 10 may collect an accelerometer signal which reflects a measurement of a motion of patient 4. In some cases, the accelerometer may collect a three-axis accelerometer signal indicative of patient 4's movements within a three-dimensional Cartesian space. For example, the accelerometer signal may include a vertical axis accelerometer signal vector, a lateral axis accelerometer signal vector, and a frontal axis accelerometer signal vector. The vertical axis accelerometer signal vector may represent an acceleration of patient 4 along a vertical axis, the lateral axis accelerometer signal vector may represent an acceleration of patient 4 along a lateral axis, and the frontal axis accelerometer signal vector may represent an acceleration of patient 4 along a frontal axis. In some cases, the vertical axis substantially extends along a torso of patient 4 from a neck of patient 4 to a waist of patient 4, the lateral axis extends across a chest of patient 4 perpendicular to the vertical axis, and the frontal axis extends outward from and through the chest of patient 4, the frontal axis being perpendicular to the vertical axis and the lateral axis.

IMD 10 may include an optical sensor. The optical sensor may, in some cases, include two or more light emitters and one or more light detectors. The optical sensor may perform one or more measurements in order to determine an oxygenation of the tissue of Patient 4. For example, the optical sensor may perform one or more tissue oxygen saturation ($StO_2$) measurements. $StO_2$ may, in some examples, represent a weighted average between Arterial blood oxygen saturation ($SaO_2$) and venous oxygen saturation ($SvO_2$). In some examples, the optical sensor may perform one or more pulse oximetry ($SpO_2$) measurements. $SpO_2$ may, in some cases, represent an approximation of $SaO_2$. Oxygen saturation (e.g., $StO_2$, $SaO_2$, $SvO_2$, and $SpO_2$) trends may be indicative of one or more patient conditions, such as heart failure, sleep apnea, or COPD, as examples. For example, a steady decline of $StO_2$ values over a period time may indicate a worsening risk of a heart failure exacerbation in a patient. As such, the IMD may perform several $StO_2$ measurements over a period of time (e.g., hours, days, weeks, or months) and the processing circuitry may identify a trend of $StO_2$ values using data from the $StO_2$ measurements. Based on the identified trend, the processing circuitry may, in some cases, identify a medical condition present in the patient or monitor a condition that is already known to be present in the patient.

During the respective $StO_2$ measurement, the light emitters of the optical sensor may output light to an area of tissue proximate to the IMD, the light including a first set of frequency components. The one or more light detectors may sense light including a second set of frequency components. The processing circuitry is configured to compare the first set of frequency components and the second set of frequency components to identify an $StO_2$ value corresponding to the respective $StO_2$ measurement, where the $StO_2$ value represents a ratio of oxygen-saturated hemoglobin located in the area of tissue to a total amount of hemoglobin located in the area of tissue.

External device 12 may be a computing device configured for use in settings such as a home, clinic, or hospital, and may further be configured to communicate with IMD 10 via wireless telemetry. For example, external device 12 may be coupled to a remote patient monitoring system, such as Carelink®, available from Medtronic plc, of Dublin, Ireland. External device 12 may, in some examples, include a programmer, an external monitor, or a consumer device such as a smart phone or tablet.

In other examples, external device 12 may be a larger workstation or a separate application within another multi-function device, rather than a dedicated computing device. For example, the multi-function device may be a notebook computer, tablet computer, workstation, one or more servers, cellular phone, personal digital assistant, or another computing device that may run an application that enables the computing device to operate as a secure device.

When external device 12 is configured for use by the clinician, external device 12 may be used to transmit instructions to IMB 10. Example instructions may include requests to set electrode combinations for sensing and any other information that may be useful for programming into IMD 10. The clinician may also configure and store operational parameters for IMD 10 within IMD 10 with the aid of external device 12. In some examples, external device 12 assists the clinician in the configuration of IMD 10 by providing a system for identifying potentially beneficial operational parameter values.

Whether external device 12 is configured for clinician or patient use, external device 12 is configured to communicate with IMB 10 and, optionally, another computing device (not illustrated in FIG. 1), via wireless communication. External device 12, for example, may communicate via near-field communication technologies (e.g., inductive coupling or other communication technologies operable at ranges less than 10-20 cm) and far-field communication technologies (e.g., radio frequency (RF) telemetry according to the 802.11 or Bluetooth® specification sets, or other communication technologies operable at ranges greater than near-field communication technologies).

Processing circuitry 14, in some examples, may include one or more processors that are configured to implement functionality and/or process instructions for execution within IMB 10, external device 12, one or more other devices, or any combination thereof. For example, processing circuitry 14 may be capable of processing instructions stored in a memory. Processing circuitry 14 may include, for example, microprocessors, digital signal processors (DSPs), application specific integrated circuits (ASICs), field-programmable gate arrays (FPGAs), or equivalent discrete or integrated logic circuitry, or a combination of any of the foregoing devices or circuitry. Accordingly, processing circuitry 14 may include any suitable structure, whether in hardware, software, firmware, or any combination thereof, to perform the functions ascribed herein to processing circuitry 14.

Processing circuitry 14 may represent processing circuitry located within any combination of IMD 10 and external device 12. In some examples, processing circuitry 14 may be entirely located within a housing of IMD 10. In other examples, processing circuitry 14 may be entirely located within a housing of external device 12. In other examples, processing circuitry 14 may be located within any combination of IMD 10, external device 12, and another device or group of devices that are not illustrated in FIG. 1. As such, techniques and capabilities attributed herein to processing circuitry 14 may be attributed to any combination of IMD 10, external device 12, and other devices that are not illustrated in FIG. 1.

A memory (not illustrated in FIG. 1) may be configured to store information within medical device system 2 during operation. The memory may include a computer-readable storage medium or computer-readable storage device. In some examples, the memory includes one or both of a short-term memory or a long-term memory. The memory may include, for example, random access memories (RAM), dynamic random access memories (DRAM), static random access memories (SRAM), magnetic discs, optical discs, flash memories, or forms of electrically programmable memories (EPROM) or electrically erasable and programmable memories (EEPROM). In some examples, the memory is used to store program instructions for execution by processing circuitry 14.

The memory may represent a memory located within any one or both of IMB 10 and external device 12. In some examples, the memory may be entirely located within a housing of IMD 10. In other examples, the memory may be entirely located within a housing of external device 12. In other examples, the memory may be located within any combination of IMD 10, external device 12, and another device or group of devices that are not illustrated in FIG. 1. As such, techniques and capabilities attributed herein to the memory may be attributed to any combination of IMD 10, external device 12, and other devices that are not illustrated in FIG. 1.

Medical device system 2 of FIG. 1 may be an example of a system for collecting a set of signals according to one or more techniques of this disclosure. For example, IMD 10 may collect an EGM via one or more electrodes. Processing circuitry 14 may include EGM analysis circuitry configured to determine one or more parameters or events (e.g., P-waves, R-waves, and T-waves) of the EGM. Cardiac signal analysis circuitry, which may be implemented as part of processing circuitry 14, may perform signal processing techniques to extract information indicating the one or more parameters or events of the EGM. An EGM measured via one or more electrodes of IMD 10 may include noise that is introduced into the EGM by a variety of cardiac and non/cardiac sources. IMD 10 may include pre-filtering circuitry configured to eliminate or reduce at least some noise in the EGM.

Processing circuitry 14 may identify, based on the accelerometer signal collected by the accelerometer of IMD 10, one or more body position changes of patient 4. Examples of body position changes which processing circuitry 14 may identify in the accelerometer signal include sit-to-stand movements, lying-to-sit movements, lying-to-stand movements, stand-to-sit movements, stand-to-lying movements, sit-to-lying movements, among other body position changes. For example, processing circuitry 14 may identify a change in a magnitude of one or more axes of the accelerometer signal and identify one or more body position changes based on the change.

In some examples, processing circuitry 14 may identify a body angle of patient 4. As used herein, the term "body angle" may refer to an angle of a torso of patient 4. For example, IMD 10 may be implanted in a torso of patient 4. As such, the accelerometer signal generated by IMD 10 reflects the body angle of the torso of the patient. A zero degree body angle, in some cases, may represent a body angle where the torso is parallel to the ground (e.g., when patient 4 is lying down. A ninety degree body angle, in some cases, may represent a body angle where the torso is perpendicular to the ground (e.g., when patient 4 is standing up or when patient 4 is sitting in an upright position). As such, processing circuitry 14 may be able to identify when patient 4 leans forward while standing or bends the torso forward while sitting by identifying a change in the body angle which is indicated by the accelerometer signal.

Processing circuitry 14 may be configured to determine a gait of patient 4 based on the accelerometer signal collected by IMD 10 while patient 4 is walking or running. For example, processing circuitry 14 may be configured to determine a step rate in which patient 4 is stepping. Additionally, or alternatively, processing circuitry 14 may be configured to calculate, based on the accelerometer signal, a stability score corresponding to the gait of patient 4.

Consequently, IMD 10 may be configured to measure a set of physiological parameters and generate an accelerometer signal which indicates one or more aspects of a physical position and movements of patient 4. Processing circuitry 14 may be configured to analyze data collected by IMD 10 in order to determine one or more statuses and risk factors of patient 4, such as a risk that patient 4 will fall within a period of time after a current time. For example, processing circuitry 14 may maintain a fall risk database which stores a plurality of sets of data each corresponding to a respective body position movement or body angle change. Processing circuitry 14 may update the fall risk database on a rolling basis. For example, processing circuitry 14 may add a set of data to the plurality of sets of data stored in the fall risk database when processing circuitry 14 detects a body position movement or body angle change. In some cases, processing circuitry 14 may remove one or more sets of data from the fall risk database.

Processing circuitry 14 may analyze the plurality of sets of data currently stored by fall risk database in order to determine a fall risk score associated with patient 4. In some examples, processing circuitry 14 may analyze the plurality of sets of data currently stored by the fall risk database on a regular basis (e.g., hourly, daily, weekly, or any other time interval). Additionally, or alternatively, processing circuitry 14 may analyze the plurality of sets of data currently stored by the fall risk database in response to receiving an instruction (e.g., from external device 12 or another user device) to analyze the data. In any case, when processing circuitry 14 determines a fall risk score associated by patient 4, processing circuitry 14 may determine the fall risk score based on one or more sets of data currently stored in the fall risk database. In some examples, the fall risk score may be referred to as a "fall risk index."

Each set of data stored by the fall risk database may include one or more portions of signals measured by IMD 10, other implantable devices, other external devices, or any combination thereof. For example, IMD 10 may collect one or more of the accelerometer signal, an EGM, one or more tissue oxygenation signals ($StO_2$ and/or $SpO_2$), and one or more other signals. When IMD 10 collects a signal, IMD 10 may collect a sequence of samples corresponding to the respective signal, and the sequence of samples may represent the signal itself. Consequently, a "portion" of the signal may represent set of consecutive samples of the signal. Each set of data stored by the fall risk database may include a portion of each signal of a set of signals, where each respective portion corresponds to a respective window of time. In some examples, the window of time corresponds to a time in which processing circuitry 14 detects a body position change or a body angle change in the accelerometer signal.

Processing circuitry 14 may be configured to identify, based on the accelerometer signal collected by IMD 10, a body position change of patient. Additionally, processing circuitry 14 may be configured to identify a time or a period of time in which the body position change occurs. Processing circuitry 14 may identify a type of the body position movement. For example, processing circuitry 14 may determine that the body position movement represents a sit-to-stand movement, a lying-to-sit movement, a lying-to-stand movement, a stand-to-sit movement, a stand-to-lying movement, a sit-to-lying movement, or another type of movement. Additionally, or alternatively, processing circuitry 14 may identify the type of the body position movement based on a body angle change associated with the body position movement. In one example, processing circuitry 14 may determine that the body position movement represents a change from a 40 degree body angle to a 90 degree body angle.

Processing circuitry 14 may set a time window based on the time or the period of time in which a body position change occurs. For example, processing circuitry 14 may set the time window to begin at a first time and end at a second time, with the first and second times being identified relative to the time or period of time in which the body position change occurs. In some examples, the first time represents a time in which the respective body position change begins. In some examples, the first time represents a time in which the respective body position change ends. In some examples, the first time represents a time between the time in which the body position change begins and the time in which the body position change ends. In some examples, the first time is a predetermined amount of time before the time or period of time in which the respective body position change occurs. In some examples, the first time is a predetermined amount of time after the time or period of time in which the respective body position change occurs. In some examples, the second time is a predetermined amount of time after the time or period of time in which the respective body position change occurs, where the second time is after the first time. In any case, the time window may include at least a portion of time following the respective body position movement.

In some cases, processing circuitry 14 may save, to the fall risk database stored in a memory (not illustrated in FIG. 1), a set of data including one or more signals corresponding to the time associated with a respective body position movement. This allows processing circuitry 14 to analyze the fall risk database in order to determine an up-to-date fall risk score corresponding to the patient 4. The set of data may include a set of signal portions. Each signal portion of the set of signal portions corresponds to a respective signal collected by IMD 10 or another device and each signal portion of the set of signal portions includes data corresponding to the window of time selected by processing circuitry 14 based on the time or period of time in which the body position change occurs. For example, the set of data may include a portion of the accelerometer signal from the first time to the second time, a portion of the EGM collected by IMD 10 from the first time to the second time, a portion of a tissue impedance signal collected by IMD 10 from the first time to the second time, and a portion of a tissue oxygen signal collected by IMD 10 from the first time to the second time.

The fall risk database may include a plurality of sets of data each corresponding to a respective body position movement and the fall risk database may include a plurality of "bins" configured to store one or more sets of data of the plurality of sets of data. For example, each bin of the plurality of bins may be associated with a respective classification of a plurality of classifications. When processing circuitry 14 identifies a body position change, processing circuitry 14 may assign one or more classifications to the identified body position change. In some examples, the plurality of classifications may include a sit-to-stand classification, a lying-to-sit classification, a lying-to-stand classification, a stand-to-sit classification, a stand-to-lying classification, and a sit-to-lying classification. In some examples, the plurality of classifications may include one or more body angle change classifications, where each body angle change classification of the one or more body angle change classifications is associated with a first range of body angles and a second range of body angles. A body angle change representing a change from a first body angle to a second body angle may fit within a body angle change classification if the first body angle falls within the first range of body angles associated with the classification and if the second body angle falls within the second range of body angles associated with the classification. In some examples, the plurality of classifications may include one or more other types of classifications such as time of day classifications.

In one example, when processing circuitry 14 detects a lying-to-stand movement which represents a body angle change from zero degrees to ninety degrees, processing circuitry 14 may assign the lying-to-stand classification and a respective body angle change classification to the detected lying-to-stand movement. When processing circuitry 14 generates a set of data corresponding to the lying-to-stand movement, processing circuitry 14 may save the set of data to each bin of the plurality of bins which is associated with a classification assigned to the lying-to-stand movement.

For each set of data generated responsive to detecting a body position change, processing circuitry 14 may save the set of data to each bin of the plurality of bins which is associated with a classification assigned to the detected body position change. This allows processing circuitry 14 to select one or more bins of the plurality of bins for a fall risk analysis. That is, processing circuitry 14 may determine a fall risk score based on one or more bins of the plurality of bins. In some examples, processing circuitry 14 may calculate a fall risk sub-score for each bin of the one or more bins and calculate a fall risk score based on each respective fall risk sub-score. In other words, processing circuitry 14 may determine a fall risk evidence level for each metric of a plurality of metrics. The "metrics" may correspond to the bins of the fall risk database. An "evidence level" may refer to an amount of evidence that patient 4 is at risk of falling. Processing circuitry 14 may determine an overall fall risk score for patient 4 based on the fall risk evidence level corresponding to each metric of the plurality of metrics.

Processing circuitry 14 may be configured to identify one or more patient parameters based on physiological signals measured by IMD 10 or other devices. In some examples, processing circuitry 14 may be configured to determine a heart rate of patient 4 based on the EGM signal measured via one or more electrodes of IMD 10. In some examples, processing circuitry 14 may determine a blood pressure of patient 4 or one or more values corresponding to the blood pressure of patient 4 based on an EGM, an impedance signal, a tissue perfusion signal (e.g., collected by an optical sensor), or any combination thereof. Additionally, or alternatively, processing circuitry 14 may determine a speed of one or more body position movements detected in the accelerometer signals, identify a stability of a gait identified in the accelerometer signal, determine one or more tissue perfusion values identified in the optical signal sensed by IMD 10 via the optical sensor, determine one or more other patient parameters based on signals collected by IMD 10 or other devices, or any combination thereof.

In some examples, to determine the heart rate of patient 4, processing circuitry 14 may determine the heart rate based on two or more R-waves detected in the EGM collected by IMD 10. For example, the EGM may include one or more R-waves each representing a ventricular depolarization of the heart of Patient 4. The rate of R-waves in the EGM may represent the heart rate of patient 4. As such, processing circuitry 14 may determine the heart rate of patient 4 over a period of time by determining the rate of R-waves in the EGM over the period of time. In some examples, the processing circuitry 14 may determine an amount of time between a first R-wave and a second R-wave consecutive to the first-wave. Based on the amount of time between the first R-wave and the second R-wave, the processing circuitry 14 may determine a heart rate of the patient 4 at the time of the second R-wave. Processing circuitry 14 may calculate the respective heart rate corresponding to each pair of consecutive R-waves in the EGM. As such, processing circuitry 14 may monitor the heart rate of patient 4 over time.

It may be expected that the blood pressure and/or the heart rate of patient 4 will increase in response to a body position movement such as a sit-to-stand movement. If the blood pressure and/or the heart rate of patient 4 do not increase by at least an expected amount in response to a body position movement, the patient 4 may experience light-headedness soon after completing the sit-to-stand movement. Such light-headedness may, in some examples, lead to patient 4 losing consciousness and/or falling. As such, it may be beneficial for processing circuitry 14 to analyze respective sets of data corresponding to each sit-to-stand movement detected in the accelerometer signal. That is, processing circuitry 14 may analyze the sit-to-stand bin in the fall risk database in order to determine a fall risk score for the patient 4. When processing circuitry 14 determines that increases in heart rate and increases in blood pressure responsive to respective sit-to-stand movements are decreasing over a period of time or have decreased below a threshold expected increase, processing circuitry 14 may determine that the patient is at risk of falling in the future. In addition to or alternatively to blood pressure and heart rate, processing circuitry 14 may analyze one or more other patient parameters indicated by respective bins of data within the fall risk database in order to determine a fall risk score of patient 4.

Although one or more techniques described herein include generating sets of data for fall risk analysis based on detecting a body position change and/or detecting a body angle change, processing circuitry 14 may also generate sets of data for fall risk analysis based on one or more other events. For example, processing circuitry 14 may generate a set of data responsive to detecting a heart event such as a pre-ventricular contraction (PVC) and save the set of data to the fall risk database. In some examples, processing circuitry 14 may assign one or more classifications to the set of data generated responsive to detecting the heart event and save the set of data to one or more bins of the fall risk database corresponding to the assigned classifications. In turn, processing circuitry 14 may analyze one or more of the bins in order to determine a fall risk score for patient 4.

As discussed above, processing circuitry 14 may monitor the accelerometer signal for one or more body position movements of patient 4 (e.g., sit-to-stand movements, lying-to-sit movements, lying-to-stand movements, standing-to-sit movements, standing-to-lying movements, and sit-to-lying movements). Additionally, or alternatively, processing circuitry 14 may monitor the accelerometer signal in order to determine a walking distance covered by patient 4. In some examples, processing circuitry 14 may determine the walking distance covered by patient 4 following each detected body position movement and store this information in a memory.

Processing circuitry 14, may determine, based on the accelerometer signal measured by IMD 10, an amount of time it takes for patient 4 to complete each body position movement detected by processing circuitry 14. For example, in the case of a sit-to-stand movement, processing circuitry 14 may determine, based on the accelerometer signal, a first time in which patient 4 begins standing up and a second time in which patient 4 finishes standing up. The difference between the first time and the second time represents the time it takes patient 4 to complete the sit-to-stand movement. Processing circuitry 14 may save the amount of time it takes to complete each detected body position movement in the fall risk database. Subsequently, processing circuitry 14 may analyze the amount of time it takes for patient 4 to complete one or more body position changes over a period of time. For example, processing circuitry 14 may analyze several sit-to-stand movements over the course of a week and determine that it is taking progressively longer for patient 4 to complete these sit-to-stand movements. In this example, processing circuitry 14 may determine that patient 4 is at an increased risk of falling. In some examples, patient 4 may perform a five times sit-to-stand (FTSTS) test, and processing circuitry 14 may save an amount of time it takes patient 4 to complete each sit-to-stand movement of the FTSTS movement.

The accelerometer signal collected by IMD 10 may indicate one or more body angle changes (e.g., one or more trunk angular displacements (TADs)). Additionally, or alternatively, the accelerometer single may indicate a gait speed (e.g., 4-meter gait speed (4MGS)) of patient 4 while patient 4 is walking or running and the accelerometer signal may indicate a gait stability of patient 4. Processing circuitry 14 may determine gait stability by tracking a variability of the accelerometer signal over a period of time. A greater variability in the accelerometer signal may represent a greater instability of the gait of patient 4 and indicate a greater risk of patient 4 falling.

Processing circuitry 14 may measure, for each time that patient 4 stands up, an amount of time that it takes for patient 4 to begin moving (e.g., begin walking) after patient 4 finishes standing up. This time between standing up and moving may be referred to herein as an expanded Timed Get-Up-and-Go (ETGUG). If the amount of time that it takes patient 4 to begin moving after standing up increases throughout a sequence of sit-to-stand movements detected in the accelerometer signal, processing circuitry 14 may determine that a risk of patient 4 falling is increasing as compared with examples in which the amount of time that it takes patient 4 to begin moving after standing up remains the same or decreases throughout a sequence of sit-to-stand movements. For example, when patient 4 pauses after standing up, this may indicate that patient 4 is experiencing lightheadedness after standing up, which increases the risk of falling as compared to when patient 4 does not experience lightheadedness after standing up.

Respective to detecting a body position movement in the accelerometer signal, processing circuitry 14 is configured to monitor blood pressure (e.g., PTT), heart rate, tissue perfusion changes, or any combination thereof over a window of time corresponding to the detecting the body position movement (e.g., a window of time extending within a range from 5 to 60 seconds following the body position movement. Specifically, processing circuitry 14 may monitor a heart rate recovery following an orthostatic challenge and monitor a blood pressure recovery following an orthostatic challenge.

In some examples, processing circuitry 14 may calculate a plurality of PTT intervals in order to track the blood pressure of patient 4 over a period of time. For example, processing circuitry 14 is configured to identify, for a set of data stored in the fall risk database, a plurality of PTT intervals. In some examples, each PTT interval of the plurality of PTT intervals represents an amount of time between a depolarization indicated by a respective portion of the EGM and an impedance feature indicated by a respective portion of the impedance signal that occurs after the respective depolarization and before a subsequent depolarization indicated by the respective portion of the EGM. In some examples, each PTT interval of the plurality of PTT intervals represents an amount of time between a depolarization indicated by a respective portion of the EGM and a tissue oxygenation feature indicated by a respective portion of a tissue oxygenation signal (e.g., $StO_2$ and/or $SpO_2$) that occurs after the respective depolarization and before a subsequent depolarization indicated by the respective portion of the EGM.

In any case, PTT may represent a parameter which indicates an amount of time which it takes blood to flow from the heart to a peripheral location within the cardiovascular system. For example, the EGM indicates a time in which the ventricles of patient 4 contract, forcing blood out of the heart. The impedance signal measured by IMD 10 indicates a tissue perfusion of tissue proximate to IMD 10. Tissue perfusion increases as blood flows to the tissue proximate to IMD 10 (e.g., during a pulse which is caused by blood flowing out of the heart of patient 4). Moreover, tissue oxygenation (e.g., $StO_2$ and/or $SpO_2$) increases as blood flows to the tissue proximate to IMD 10 (e.g., during a pulse). Consequently, an amount of time between an R-wave detected in the EGM and an impedance signal feature detected in the impedance signal collected by IMD 10 may represent a PTT interval. Additionally, or alternatively, an amount of time between an R-wave detected in the EGM and a tissue oxygenation feature detected in the tissue oxygenation signal may represent a PTT interval. PTT intervals may have an inverse relationship with blood pressure. For example, a shorter PTT interval represents a greater flow speed of blood, which indicates a higher blood pressure. Alternatively, a longer PTT interval represents a lower flow speed of blood, which indicates a lower blood pressure. In any case, a relationship may exist between blood pressure and PTT intervals of patient 4. As such, PTT interval values be used by processing circuitry 14 as a stand-in or a proxy for blood pressure values.

Processing circuitry 14 may determine, based on a plurality of PTT intervals corresponding to a respective set of data, a PTT change value corresponding to a time window associated with the set of data. The PTT change value represents a change between one or more PTT intervals in a first section of the respective time window and one or more PTT intervals in a second section of the time window. Processing circuitry 14 may calculate, based on the PTT change value corresponding one or more sets of data stored in the fall risk database, a fall risk score corresponding to patient 4.

Although in one example IMD 10 takes the form of an ICM, in other examples, IMD 10 takes the form of any combination of implantable cardioverter defibrillators (ICDs) with intravascular or extravascular leads, pacemakers, cardiac resynchronization therapy devices (CRT-Ds), neuromodulation devices, left ventricular assist devices (LVADs), implantable sensors, orthopedic devices, or drug pumps, as examples. Moreover, although described in the context of an IMD, the techniques of this disclosure may be implemented by systems that additionally or alternatively include one or more external sensor devices, such as a wearable patient monitor, smartwatch, or Fitbit.

Figure 2:
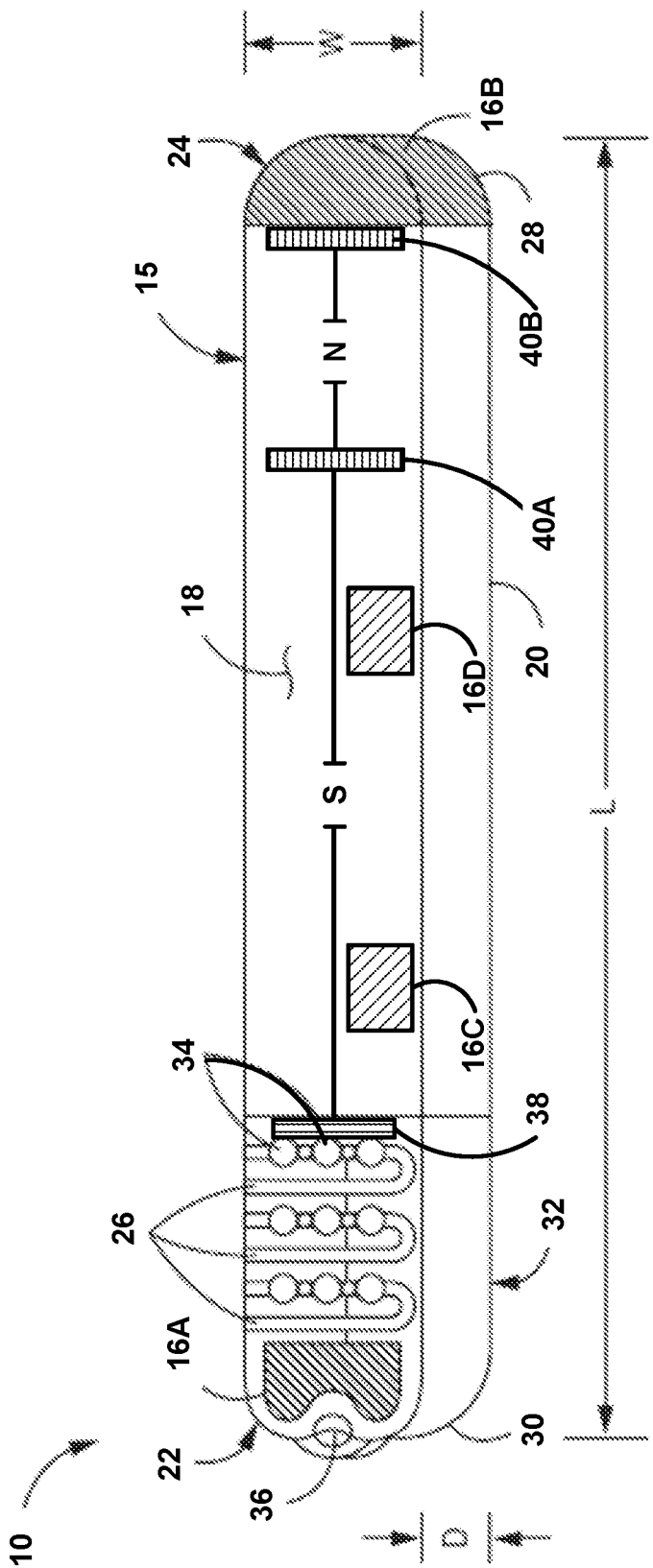
FIG. 2 is a conceptual drawing illustrating an example configuration of the implantable medical device (IMD) of the medical device system of FIG. 1, in accordance with one or more techniques described herein.

FIG. 2 is a conceptual drawing illustrating an example configuration of IMD 10 of the medical device system 2 of FIG. 1, in accordance with one or more techniques described herein. In the example shown in FIG. 2, IMD 10 may include a leadless, subcutaneously-implantable monitoring device having housing 15, proximal electrode 16A, and distal electrode 16B. Housing 15 may further include first major surface 18, second major surface proximal end 22, and distal end 24. In some examples, IMD 10 may include one or more additional electrodes 16C, 16D positioned on one or both of major surfaces 18,20 of IMD 10. Housing 15 encloses electronic circuitry located inside the IMD 10, and protects the circuitry contained therein from fluids such as body fluids. In some examples, electrical feedthroughs provide electrical connection of electrodes 16A-16D, and antenna 26, to circuitry within housing 15. In some examples, electrode 16B may be formed from an uninsulated portion of conductive housing 15.

In the example shown in FIG. 2, IMD 10 is defined by a length L, a width W, and thickness or depth D. In this example, IMD 10 is in the form of an elongated rectangular prism in which length L is significantly greater than width W, and in which width W is greater than depth D. However, other configurations of IMD 10 are contemplated, such as those in which the relative proportions of length L, width W, and depth D vary from those described and shown in FIG. 2. In some examples, the geometry of the IMD 10, such as the width W being greater than the depth D, may be selected to allow IMD 10 to be inserted under the skin of the patient using a minimally invasive procedure and to remain in the desired orientation during insertion. In addition, IMD 10 may include radial asymmetries (e.g., the rectangular shape) along a longitudinal axis of IMD 10, which may help maintain the device in a desired orientation following implantation.

In some examples, a spacing between proximal electrode 16A and distal electrode 16B may range from about 30-55 mm, about 35-55 mm, or about 40-55 mm, or more generally from about 25-60 mm. Overall, IMD 10 may have a length L of about 20-30 mm, about 40-60 mm, or about 45-60 mm. In some examples, the width W of major surface 18 may range from about 3-10 mm, and may be any single width or range of widths between about 3-10 mm. In some examples, a depth D of IMD 10 may range from about 2-9 mm. In other examples, the depth D of IMD 10 may range from about 2-5 mm, and may be any single or range of depths from about 2-9 mm. In any such examples, IMD 10 is sufficiently compact to be implanted within the subcutaneous space of patient 4 in the region of a pectoral muscle.

IMD 10, according to an example of the present disclosure, may have a geometry and size designed for ease of implant and patient comfort. Examples of IMD 10 described in this disclosure may have a volume of 3 cubic centimeters ($cm^3$) or less, 1.5 $cm^3$ or less, or any volume therebetween. In addition, in the example shown in FIG. 2, proximal end 22 and distal end 24 are rounded to reduce discomfort and irritation to surrounding tissue once implanted under the skin of patient 4.

In the example shown in FIG. 2, first major surface 18 of IMD 10 faces outward towards the skin, when IMD 10 is inserted within patient 4, whereas second major surface 20 faces inward toward musculature of patient 4. Thus, first and second major surfaces 18, 20 may face in directions along a sagittal axis of patient 4 (see FIG. 1), and this orientation may be maintained upon implantation due to the dimensions of IMD 10.

Proximal electrode 16A and distal electrode 16B may be used to sense cardiac EGMs (e.g., cardiac ECGs) when IMD 10 is implanted subcutaneously in patient 4. In some examples, processing circuitry of IMD 10 also may determine whether cardiac EGMs of patient 4 are indicative of arrhythmia or other abnormalities, which processing circuitry of IMD 10 may evaluate in determining whether a medical condition (e.g., heart failure, sleep apnea, or COPD) of patient 4 has changed. The cardiac EGMs may be stored in a memory of the IMD 10. In some examples, data derived from the EGMs may be transmitted via integrated antenna 26 to another medical device, such as external device 12. In some examples, one or both of electrodes 16A and 16B also may be used by IMD 10 to collect one or more impedance signals (e.g., a subcutaneous tissue impedance) during impedance measurements performed by IMD 10. In some examples, such impedance values detected by IMD 10 may reflect a resistance value associated with a contact between electrodes 16A, 16B, and target tissue of patient 4. Additionally, in some examples, electrodes 16A, 16B may be used by communication circuitry of IMD 10 for tissue conductance communication (TCC) communication with external device 12 or another device.

In the example shown in FIG. 2, proximal electrode 16A is in close proximity to proximal end 22, and distal electrode 16B is in close proximity to distal end 24 of IMD 10. In this example, distal electrode 16B is not limited to a flattened, outward facing surface, but may extend from first major surface 18, around rounded edges 28 or end surface 30, and onto the second major surface 20 in a three-dimensional curved configuration. As illustrated, proximal electrode 16A is located on first major surface 18 and is substantially flat and outward facing. However, in other examples not shown here, proximal electrode 16A and distal electrode 16B both may be configured like proximal electrode 16A shown in FIG. 2, or both may be configured like distal electrode 16B shown in FIG. 2. In some examples, additional electrodes 16C and 16D may be positioned on one or both of first major surface 18 and second major surface 20, such that a total of four electrodes are included on IMD 10. Any of electrodes 16A-16D may be formed of a biocompatible conductive material. For example, any of electrodes 16A-16D may be formed from any of stainless steel, titanium, platinum, iridium, or alloys thereof. In addition, electrodes of IMD 10 may be coated with a material such as titanium nitride or fractal titanium nitride, although other suitable materials and coatings for such electrodes may be used.

In the example shown in FIG. 2, proximal end 22 of IMD 10 includes header assembly 32 having one or more of proximal electrode 16A, integrated antenna 26, anti-migration projections 34, and suture hole 36. Integrated antenna 26 is located on the same major surface (e.g., first major surface 18) as proximal electrode 16A, and may be an integral part of header assembly 32. In other examples, integrated antenna 26 may be formed on the major surface opposite from proximal electrode 16A, or, in still other examples, may be incorporated within housing 15 of IMD 10. Antenna 26 may be configured to transmit or receive electromagnetic signals for communication. For example, antenna 26 may be configured to transmit to or receive signals from a programmer via inductive coupling, electromagnetic coupling, tissue conductance, Near Field Communication (NFC), Radio Frequency Identification (RFID), Bluetooth®, Wi-Fi®, or other proprietary or non-proprietary wireless telemetry communication schemes. Antenna 26 may be coupled to communication circuitry of IMD 10, which may drive antenna 26 to transmit signals to external device 12 and may transmit signals received from external device 12 to processing circuitry of IMD 10 via communication circuitry.

IMD 10 may include several features for retaining IMD 10 in position once subcutaneously implanted in patient 4. For example, as shown in FIG. 2, housing 15 may include anti-migration projections 34 positioned adjacent integrated antenna 26. Anti-migration projections 34 may include a plurality of bumps or protrusions extending away from first major surface 18 and may help prevent longitudinal movement of IMD 10 after implantation in patient 4. In other examples, anti-migration projections 34 may be located on the opposite major surface as proximal electrode 16A and/or integrated antenna 26. In addition, in the example shown in FIG. 2 header assembly 32 includes suture hole 36, which provides another means of securing IMD 10 to the patient to prevent movement following insertion. In the example shown, suture hole 36 is located adjacent to proximal electrode 16A. In some examples, header assembly 32 may include a molded header assembly made from a polymeric or plastic material, which may be integrated or separable from the main portion of IMD 10.

Electrodes 16A and 16B may be used to sense cardiac EGMs, as described above. Additional electrodes 16C and 16D may be used to sense subcutaneous tissue impedance, in addition to or instead of electrodes 16A, 16B, in some examples. In some examples, processing circuitry of IMD 10 may determine an impedance value of patient 4 based on signals received from at least two of electrodes 16A-16D. For example, processing circuitry of IMD 10 may generate one of a current or voltage signal, deliver the signal via a selected two or more of electrodes 16A-16D, and measure the resulting other of current or voltage. Processing circuitry of IMD 10 may determine an impedance value based on the delivered current or voltage and the measured voltage or current.

In the example shown in FIG. 2, IMD 10 includes light emitter(s) 38 and a proximal light detector 40A and a distal light detector 40B (collectively, "light detectors 40") positioned on housing 15 of IMD 10. Light detector 40A may be positioned at a distance S from light emitter(s) 38, and a distal light detector 40B positioned at a distance S+N from light emitter(s) 38. In other examples, IMD 10 may include only one of light detectors 40A, 40B, or may include additional light emitters and/or additional light detectors. Collectively, light emitter(s) 38 and light detectors 40A, 40B may include an optical sensor, which may be used in the techniques described herein to determine $StO_2$ or $SpO_2$ values of patient 4. Although light emitter(s) 38 and light detectors 40A, 40B are described herein as being positioned on housing 15 of IMD 10, in other examples, one or more of light emitter(s) 38 and light detectors 40A, 40B may be positioned, on a housing of another type of IMD within patient 4, such as a transvenous, subcutaneous, or extravascular pacemaker or ICD, or connected to such a device via a lead. Light emitter(s) 38 include a light source, such as an LED, that may emit light at one or more wavelengths within the visible (VIS) and/or near-infrared (NIR) spectra. For example, light emitter(s) 38 may emit light at one or more of about 660 nanometer (nm), 720 nm, 760 nm, 800 nm, or at any other suitable wavelengths.

In some examples, techniques for determining $StO_2$ may include using light emitter(s) 38 to emit light at one or more VIS wavelengths (e.g., approximately 660 nm) and at one or more NIR wavelengths (e.g., approximately 850-890 nm). The combination of VIS and NIR wavelengths may help enable processing circuitry of IMD 10 to distinguish oxygenated hemoglobin from deoxygenated hemoglobin in the tissue of patient 4, since as hemoglobin becomes less oxygenated, an attenuation of VIS light increases and an attenuation of NIR decreases. By comparing the amount of VIS light detected by light detectors 40A, 40B to the amount of NIR light detected by light detectors 40A, 40B, processing circuitry of IMD 10 may determine the relative amounts of oxygenated and deoxygenated hemoglobin in the tissue of patient 4. For example, if the amount of oxygenated hemoglobin in the tissue of patient 4 decreases, the amount of VIS light detected by light detectors 40A, 40B increases and the amount of NIR light detected by light detectors 40B decreases. Similarly, if the amount of oxygenated hemoglobin in the tissue of patient 4 increases, the amount of VIS light detected by light detectors 40A, 40B decreases and the amount of NIR light detected by light detectors 40A, 40B increases.

As shown in FIG. 2, light emitter(s) 38 may be positioned on header assembly 32, although, in other examples, one or both of light detectors 40A, 40B may additionally or alternatively be positioned on header assembly 32. In some examples, light emitter(s) 38 may be positioned on a medial section of IMD 10, such as part way between proximal end 22 and distal end 24. Although light emitter(s) 38 and light detectors 40A, 40B are illustrated as being positioned on first major surface 18, light emitter(s) 38 and light detectors 40A, 40B alternatively may be positioned on second major surface 20. In some examples, IMD may be implanted such that light emitter(s) 38 and light detectors 40A, 40B face inward when IMD is implanted, toward the muscle of patient 4, which may help minimize interference from background light coming from outside the body of patient 4. Light detectors 40A, 40B may include a glass or sapphire window, such as described below with respect to FIG. 4B, or may be positioned beneath a portion of housing 15 of IMD 10 that is made of glass or sapphire, or otherwise transparent or translucent.

Light emitter(s) 38 may emit light into a target site of patient 4 during a technique for determining an $StO_2$ value of patient 4. The target site may generally include the interstitial space around IMD 10 when IMD 10 is implanted in patient 4. Light emitter(s) 38 may emit light directionally in that light emitter(s) 38 may direct the signal to a side of IMD 10, such as when light emitter(s) 38 are disposed on the side of IMD 10 that includes first major surface 18. The target site may include the subcutaneous tissue adjacent IMD 10 within patient 4.

Techniques for determining an $StO_2$ value may be based on the optical properties of blood-perfused tissue that change depending upon the relative amounts of oxygenated and deoxygenated hemoglobin in the microcirculation of tissue. These optical properties are due, at least in part, to the different optical absorption spectra of oxygenated and deoxygenated hemoglobin. Thus, the oxygen saturation level of the patient's tissue may affect the amount of light that is absorbed by blood within the tissue adjacent IMD 10, and the amount of light that is reflected by the tissue. Light detectors 40A, 40B each may receive light from light emitter(s) 38 that is reflected by the tissue, and generate electrical signals indicating the intensities of the light detected by light detectors 40A, 40B. Processing circuitry of IMD 10 then may evaluate the electrical signals from light detectors 40A, 40B in order to determine an $StO_2$ value of patient 4.

In some examples, a difference between the electrical signals generated by light detectors 40A, 40B may enhance an accuracy of the $StO_2$ value determined by IMD 10. For example, because tissue absorbs some of the light emitted by light emitter(s) 38, the intensity of the light reflected by tissue becomes attenuated as the distance (and amount of tissue) between light emitter(s) 38 and light detectors 40A, 40B increases. Thus, because light detector 40B is positioned further from light emitter(s) 38 (at distance S+N) than light detector 40A (at distance S), the intensity of light detected by light detector 40B should be less than the intensity of light detected by light detector 40A. Due to the close proximity of detectors 40A, 40B to one another, the difference between the intensity of light detected by light detector 40A and the intensity of light detected by light detector 40B should be attributable only to the difference in distance from light emitter(s) 38. In some examples, processing circuitry of IMD 10 may use the difference between the electrical signals generated by light detectors 40A, 40B, in addition to the electrical signals themselves, in determining an $StO_2$ value of patient 4.

In some examples, IMD 10 may include one or more additional sensors, such as one or more accelerometers (not illustrated in FIG. 2). Such accelerometers may be 3D accelerometers configured to generate signals indicative of one or more types of movement of the patient, such as gross body movement (e.g., motion) of the patient, patient posture, movements associated with the beating of the heart, or coughing, rales, or other respiration abnormalities. One or more of the parameters monitored by IMD 10 (e.g., impedance, EGM) may fluctuate in response to changes in one or more such types of movement. For example, changes in parameter values sometimes may be attributable to increased patient motion (e.g., exercise or other physical motion as compared to immobility) or to changes in patient posture, and not necessarily to changes in a medical condition. Thus, in some methods of identifying or tracking a medical condition of patient 4, it may be advantageous to account for such fluctuations when determining whether a change in a parameter is indicative of a change in a medical condition.

In some examples, IMD 10 may perform an $SpO_2$ measurement using light emitter(s) 38 and light detectors 40. For example, IMD 10 may perform $SpO_2$ measurements by using light emitter(s) 38 to emit light at one or more VIS wavelengths, one more NIR wavelengths, or a combination of one or more VIS wavelengths and one more NIR wavelengths. By comparing the amount of VIS light detected by light detectors 40A, 40B to the amount of NIR light detected by light detectors 40A, 40B, processing circuitry of IMD 10 may determine the relative amounts of oxygenated and deoxygenated hemoglobin in the tissue of patient 4. For example, if the amount of oxygenated hemoglobin in the tissue of patient 4 decreases, the amount of VIS light detected by light detectors 40A, 40B increases and the amount of NIR light detected by light detectors 40A, 40B decreases. Similarly, if the amount of oxygenated hemoglobin in the tissue of patient 4 increases, the amount of VIS light detected by light detectors 40A, 40B decreases and the amount of NIR light detected by light detectors 40A, 40B increases.

Although $SpO_2$ measurements and $StO_2$ measurements may both employ the optical sensor (e.g., light emitter(s) 38 and light detectors 40) of IMD 10 to emit and sense light, $SpO_2$ measurements may consume significantly more energy than $StO_2$ measurements. In some examples, an $SpO_2$ measurement may consume up to 3 orders of magnitude (1,000 times) more power than an $StO_2$ measurement. Reasons for the energy consumption disparity include that $SpO_2$ measurements may require light emitter(s) 38 to be activated for up to 30 seconds, where $StO_2$ measurements may require light emitter(s) 38 to be activated for up to 5 seconds. Additionally, $SpO_2$ measurements may require a sampling rate of up to 70 Hz, whereas $StO_2$ measurements may require a sampling rate of up to 4 Hz.

Figure 3:
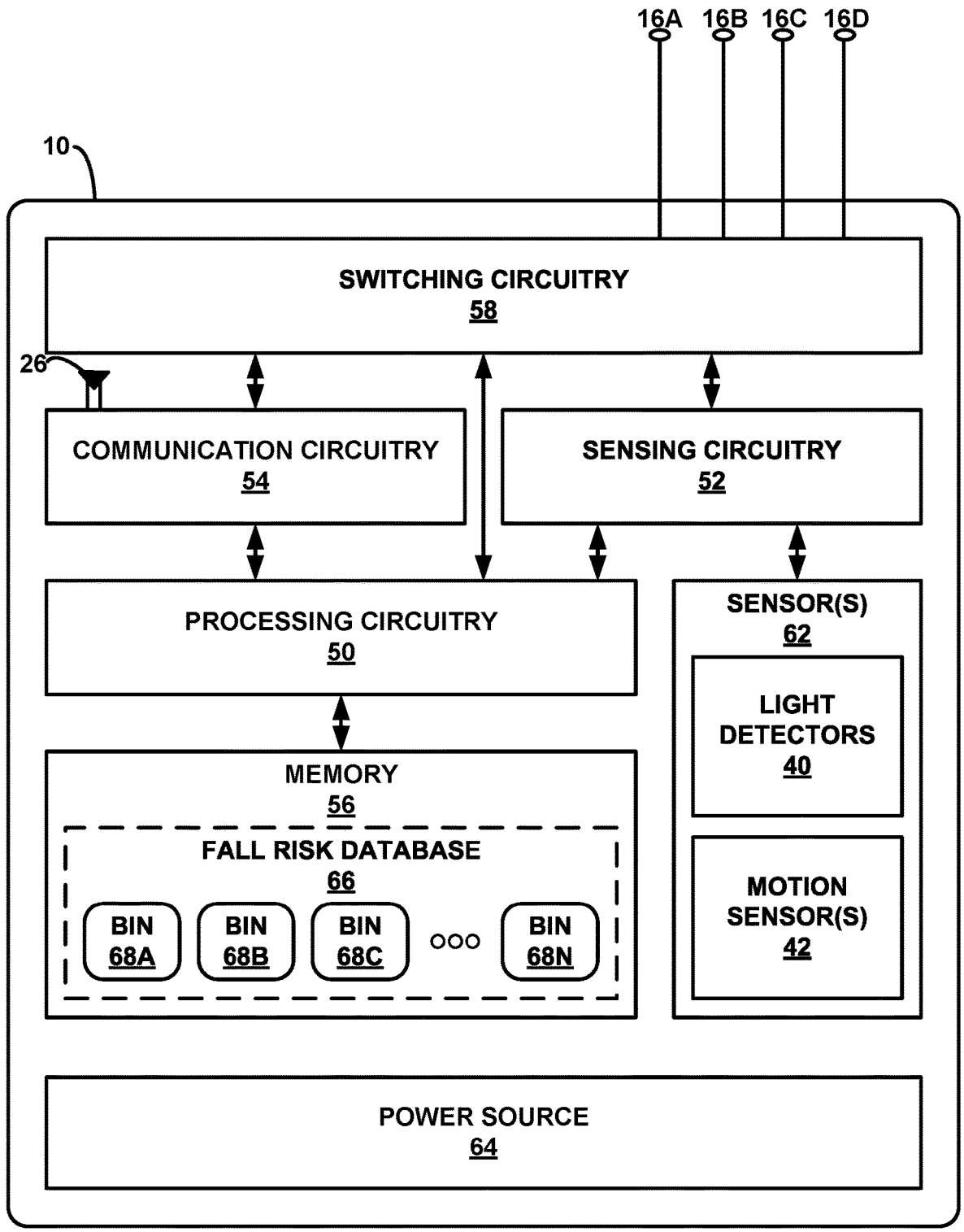
FIG. 3 is a functional block diagram illustrating an example configuration of the IMD of FIGS. 1 and 2, in accordance with one or more techniques described herein.

FIG. 3 is a functional block diagram illustrating an example configuration of IMD of FIGS. 1 and 2, in accordance with one or more techniques described herein. As seen in FIG. 3, IMD 10 includes electrodes 16A-16D (collectively, "electrodes 16"), antenna 26, processing circuitry 50, sensing circuitry 52, communication circuitry 54, memory 56, switching circuitry 58, sensors 62 including light detectors 40 and motion sensor(s) 42, and power source 64. Memory 56 is configured to store fall risk database 66 which includes bins 68A-68N (collectively, "bins 68"). Although memory 56 is illustrated as storing fall risk database 66, one or more other memories may additionally or alternatively store at least a portion of fall risk database 66. For example, a memory of external device 12 of FIG. 1 may be configured to store at least a portion of fall risk database 66. In some examples, another memory may be configured to store at least a portion of fall risk database 66.

Processing circuitry 50 may include fixed function circuitry and/or programmable processing circuitry. Processing circuitry 50 may include, for example, microprocessors, DSPs, ASICs, FPGAs, equivalent discrete or integrated logic circuitry, or a combination of any of the foregoing devices or circuitry. Accordingly, processing circuitry 50 may include any suitable structure, whether in hardware, software, firmware, or any combination thereof, to perform the functions ascribed herein to IMD 10. In some examples, processing circuitry may represent at least a portion of processing circuitry 14 of FIG. 1, but this is not required. In some examples, processing circuitry 50 may be separate from processing circuitry 14 of FIG. 1.

Sensing circuitry 52 and communication circuitry 54 may be selectively coupled to electrodes 16 via switching circuitry 58, which may be controlled by processing circuitry Sensing circuitry 52 may monitor signals from electrodes 16 in order to monitor electrical activity of heart (e.g., to produce an EGM), and/or subcutaneous tissue impedance, the impedance being indicative of at least some aspects of patient 4's cardiac activity and/or respiratory patterns. Sensing circuitry 52 also may monitor signals from sensors 62, which may include light detectors 40, motion sensor(s) 42, and any additional sensors that may be positioned on IMD 10. In some examples, sensing circuitry 52 may include one or more filters and amplifiers for filtering and amplifying signals received from one or more of electrodes 16 and/or sensor(s) 62.

Communication circuitry 54 may include any suitable hardware, firmware, software or any combination thereof for communicating with another device, such as external device 12 or another device or sensor, such as a pressure sensing device. Under the control of processing circuitry 50, communication circuitry 54 may receive downlink telemetry from, as well as send uplink telemetry to, external device 12 or another device with the aid of an internal or external antenna, e.g., antenna 26. In addition, processing circuitry 50 may communicate with a networked computing device via an external device (e.g., external device 12) and a computer network, such as the Medtronic CareLink® Network developed by Medtronic, plc, of Dublin, Ireland.

A clinician or other user may retrieve data from IMD 10 using external device 12, or by using another local or networked computing device configured to communicate with processing circuitry 50 via communication circuitry 54. The clinician may also program parameters of IMD 10 using external device 12 or another local or networked computing device.

In some examples, memory 56 includes computer-readable instructions that, when executed by processing circuitry 50, cause IMD 10 and processing circuitry 50 to perform various functions attributed to IMD 10 and processing circuitry 50 herein. Memory 56 may include one or both of a short-term memory or a long-term memory. The memory may include, for example, RAM, DRAM, SRAM, magnetic discs, optical discs, flash memories, or forms of EPROM or EEPROM. In some examples, the memory is used to store program instructions for execution by processing circuitry 50.

Memory 56 is configured to store at least a portion of fall risk database 66. Fall risk database 66 includes a plurality of sets of data. Each set of data of the plurality of sets of data may, in some examples, correspond to an event detected in data collected by IMD 10. For example, at least one of the plurality of sets of data may correspond to a body position change or a body angle change detected in the accelerometer signal which is collected by IMD 10. Additionally, or alternatively, at least one of the plurality of sets of data may correspond to a cardiac event detected in one or more signals (e.g., EMG, impedance signals, optical signals, or any combination thereof) collected by IMD 10.

In some examples, each set of data of the plurality of sets of data includes respective portions of one or more signals, where the respective portions of the one or more signals correspond to a respective time window. For example, a first set of data may include a set of signals corresponding to a first time window and a second set of data may include a set of signals corresponding to a second time window, where the first time window is different than the second time window. The first set of data may include at least one of the same signals as the second set of data. As such, the first set of data and the second set of data may include at least one overlapping signal, although the first set of data corresponds to the first time window and the second set of data corresponds to the second time window.

Fall risk database 66 includes bins 68. In some examples, each of bins 68 may correspond to one or more classifications. A set of data may be sorted into bins 68 based on one or more classifications associated with the set of data. For example, bin 68A may be associated with a sit-to-stand classification and bin 68B may be associated with a lying-to-stand classification. Bins 68C-68N may each be associated with one or more of a plurality of classifications. When first set of data is associated with the sit-to-stand classification, memory 56 may store the first set of data in bin 68A. In some examples, processing circuitry (e.g., processing circuitry 14 of FIG. 1) may analyze one or more of bins 68 in order to determine a fall risk score associated with patient 4.

Power source 64 is configured to deliver operating power to the components of IMD 10. Power source 64 may include a battery and a power generation circuit to produce the operating power. In some examples, the battery is rechargeable to allow extended operation. In some examples, recharging is accomplished through proximal inductive interaction between an external charger and an inductive charging coil within external device 12. Power source 64 may include any one or more of a plurality of different battery types, such as nickel cadmium batteries and lithium ion batteries. A non-rechargeable battery may be selected to last for several years, while a rechargeable battery may be inductively charged from an external device, e.g., on a daily or weekly basis.

Figure 4A:
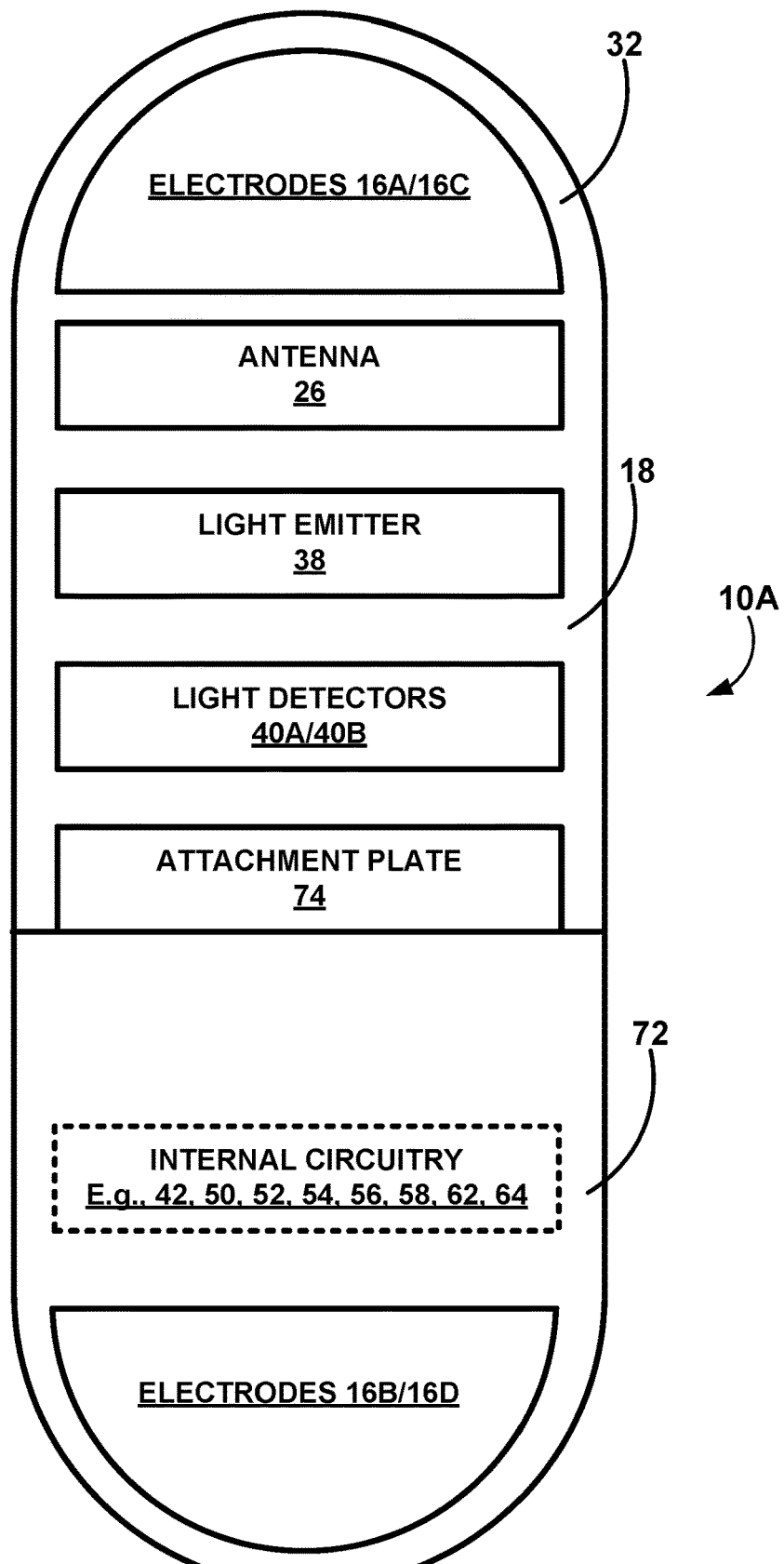
FIGS. 4A and 4B illustrate two additional example IMDs that may be substantially similar to the IMD of FIGS. 1-3, but which may include one or more additional features, in accordance with one or more techniques described herein.
Figure 4B:
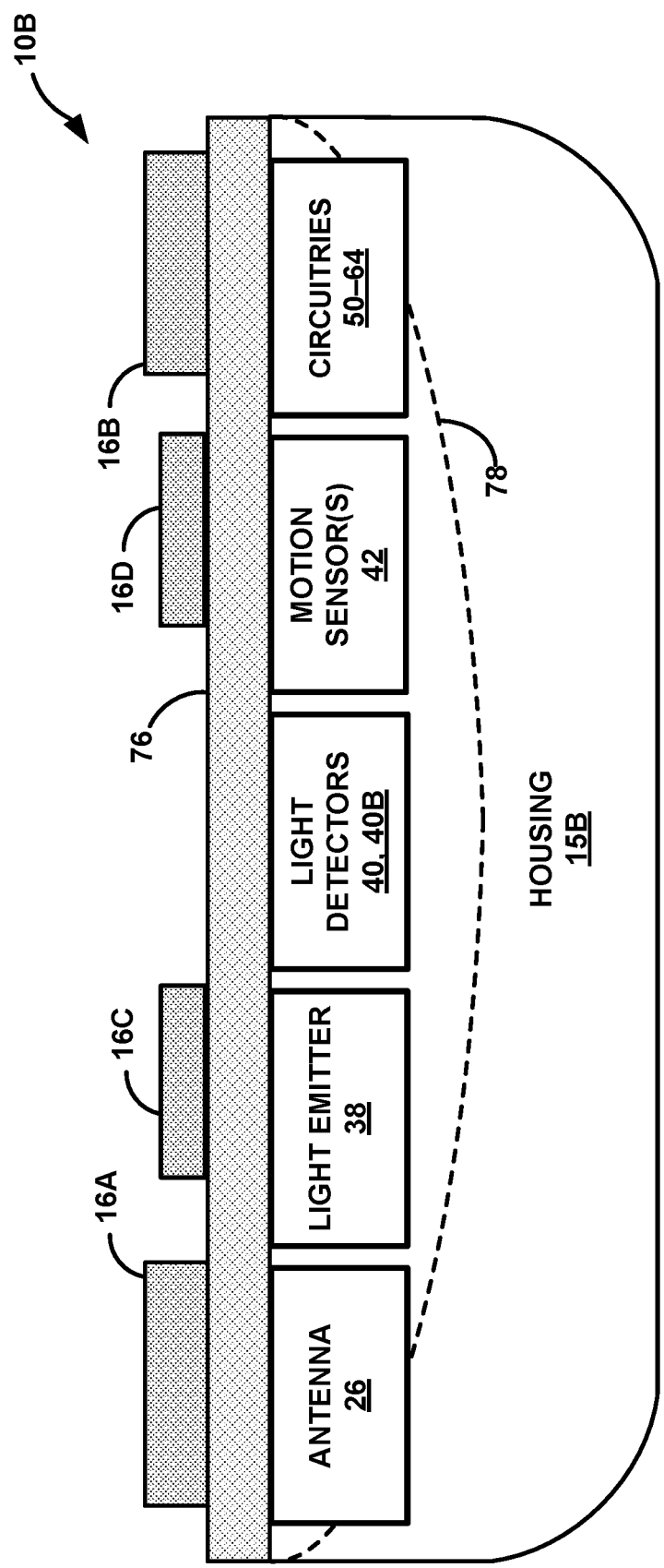

FIGS. 4A and 4B illustrate two additional example IMDs that may be substantially similar to IMD 10 of FIGS. 1-3, but which may include one or more additional features, in accordance with one or more techniques described herein. The components of FIGS. 4A and 4B may not necessarily be drawn to scale, but instead may be enlarged to show detail. FIG. 4A is a block diagram of a top view of an example configuration of an IMD 10A. FIG. 4B is a block diagram of a side view of example IMD 10B, which may include an insulative layer as described below.

FIG. 4A is a conceptual drawing illustrating another example IMD 10A that may be substantially similar to IMD 10 of FIG. 1. In addition to the components illustrated in FIGS. 1-3, the example of IMD 10 illustrated in FIG. 4A also may include a body portion 72 and an attachment plate 74. Attachment plate 74 may be configured to mechanically couple header assembly 32 to body portion 72 of IMD 10A. Body portion 72 of IMD 10A may be configured to house one or more of the internal components of IMD 10 illustrated in FIG. 3, such as one or more of processing circuitry 50, sensing circuitry 52, communication circuitry 54, memory 56, switching circuitry 58, internal components of sensors 62, and power source 64. In some examples, body portion 72 may be formed of one or more of titanium, ceramic, or any other suitable biocompatible materials.

FIG. 4B is a conceptual drawing illustrating another example IMD 10B that may include components substantially similar to IMD 10 of FIG. 1. In addition to the components illustrated in FIGS. 1-3, the example of IMD 10B illustrated in FIG. 4B also may include a wafer-scale insulative cover 76, which may help insulate electrical signals passing between electrodes 16A-16D and/or light detectors 40A, 40B on housing 15B and processing circuitry 50. In some examples, insulative cover 76 may be positioned over an open housing to form the housing for the components of IMD 10B. One or more components of IMD (e.g., antenna 26, light emitter 38, light detectors 40A, 40B, processing circuitry 50, sensing circuitry 52, communication circuitry 54, switching circuitry 58, and/or power source 64) may be formed on a bottom side of insulative cover 76, such as by using flip-chip technology. Insulative cover 76 may be flipped onto a housing 15B. When flipped and placed onto housing 15B, the components of IMD 10B formed on the bottom side of insulative cover 76 may be positioned in a gap 78 defined by housing 15B.

Figure 5:
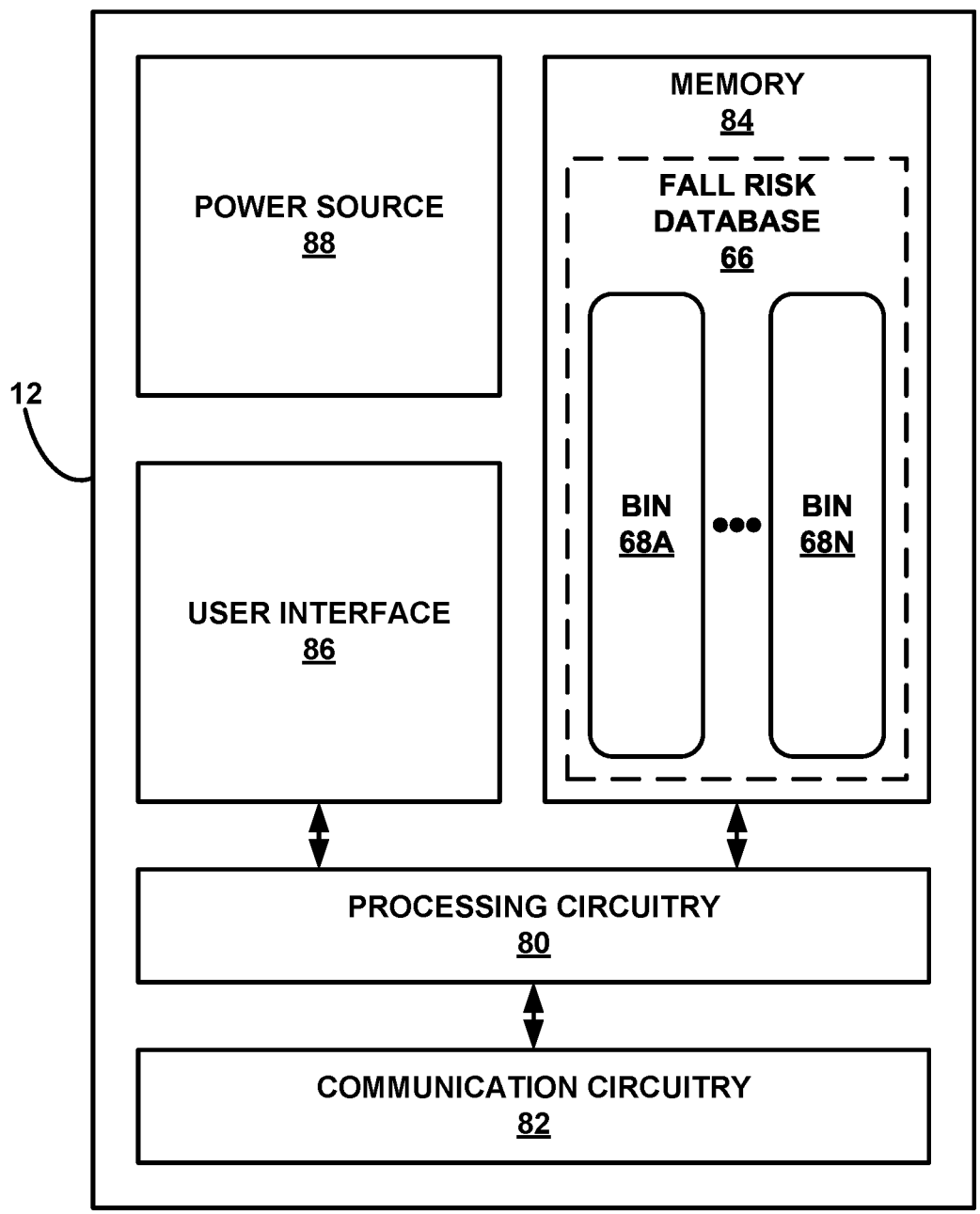
FIG. 5 is a block diagram illustrating an example configuration of components of external device, in accordance with one or more techniques of this disclosure.

FIG. 5 is a block diagram illustrating an example configuration of components of external device 12, in accordance with one or more techniques of this disclosure. In the example of FIG. 5, external device 12 includes processing circuitry 80, communication circuitry 82, memory 84, user interface 86, and power source 88. Memory 84 is configured to store fall risk database 66 which includes bins 68. Although Memory 86 is illustrated as storing fall risk database 66, one or more other memories may additionally or alternatively store at least a portion of fall risk database 66. For example, memory 56 of IMD 10 may be configured to store at least a portion of fall risk database 66. In some examples, another memory may be configured to store at least a portion of fall risk database 66.

Processing circuitry 80 may include fixed function circuitry and/or programmable processing circuitry. Processing circuitry 80 may include, for example, microprocessors, DSPs, ASICs, FPGAs, equivalent discrete or integrated logic circuitry, or a combination of any of the foregoing devices or circuitry. Accordingly, processing circuitry 80 may include any suitable structure, whether in hardware, software, firmware, or any combination thereof, to perform the functions ascribed herein to external device 12. In some examples, processing circuitry 80 may represent at least a portion of processing circuitry 14 of FIG. 1, but this is not required. In some examples, processing circuitry 50 may be separate from processing circuitry 14 of FIG. 1.

Communication circuitry 82 may include any suitable hardware, firmware, software or any combination thereof for communicating with another device, such as IMD 10. Under the control of processing circuitry 80, communication circuitry 82 may receive downlink telemetry from, as well as send uplink telemetry to, IMD 10, or another device.

In some examples, memory 84 includes computer-readable instructions that, when executed by processing circuitry 80, cause external device 12 and processing circuitry 80 to perform various functions attributed to IMD 10 and processing circuitry 80 herein. Memory 84 may include one or both of a short-term memory or a long-term memory. The memory may include, for example, RAM, DRAM, SRAM, magnetic discs, optical discs, flash memories, or forms of EPROM or EEPROM. In some examples, the memory is used to store program instructions for execution by processing circuitry 80. Memory 84 may be used by software or applications running on external device 12 to temporarily store information during program execution. In some examples, fall risk database 66 may include one or more sets of data received from IMD 10 and sorted into bins 68.

Data exchanged between external device 12 and IMB 10 may include operational parameters. External device 12 may transmit data including computer readable instructions which, when implemented by IMD 10, may control IMD 10 to change one or more operational parameters and/or export collected data. For example, processing circuitry 80 may transmit an instruction to IMB 10 which requests IMD 10 to export collected data (e.g., data corresponding to one or both of an ECG signal and an accelerometer signal) to external device 12. In turn, external device 12 may receive the collected data from IMD 10 and store the collected data in memory 84. Additionally, or alternatively, processing circuitry 80 may export instructions to IMD 10 requesting IMD 10 to update electrode combinations for stimulation or sensing.

A user, such as a clinician or patient 4, may interact with external device 12 through user interface 86. User interface 86 includes a display (not shown), such as an LCD or LED display or other type of screen, with which processing circuitry 80 may present information related to IMD 10 (e.g., EGM signals obtained from at least one electrode or at least one electrode combination, impedance signals, motion signals, a fall risk score associated with patient 4 over time, or any combination thereof). In addition, user interface 86 may include an input mechanism to receive input from the user. The input mechanisms may include, for example, any one or more of buttons, a keypad (e.g., an alphanumeric keypad), a peripheral pointing device, a touch screen, or another input mechanism that allows the user to navigate through user interfaces presented by processing circuitry 80 of external device 12 and provide input. In other examples, user interface 86 also includes audio circuitry for providing audible notifications, instructions or other sounds to patient 4, receiving voice commands from patient 4, or both. Memory 84 may include instructions for operating user interface 86 and for managing power source 88.

Power source 88 is configured to deliver operating power to the components of external device 12. Power source 88 may include a battery and a power generation circuit to produce the operating power. In some examples, the battery is rechargeable to allow extended operation. Recharging may be accomplished by electrically coupling power source 88 to a cradle or plug that is connected to an alternating current (AC) outlet. In addition, recharging may be accomplished through proximal inductive interaction between an external charger and an inductive charging coil within external device 12. In other examples, traditional batteries (e.g., nickel cadmium or lithium ion batteries) may be used. In addition, external device 12 may be directly coupled to an alternating current outlet to operate.

Figure 6:
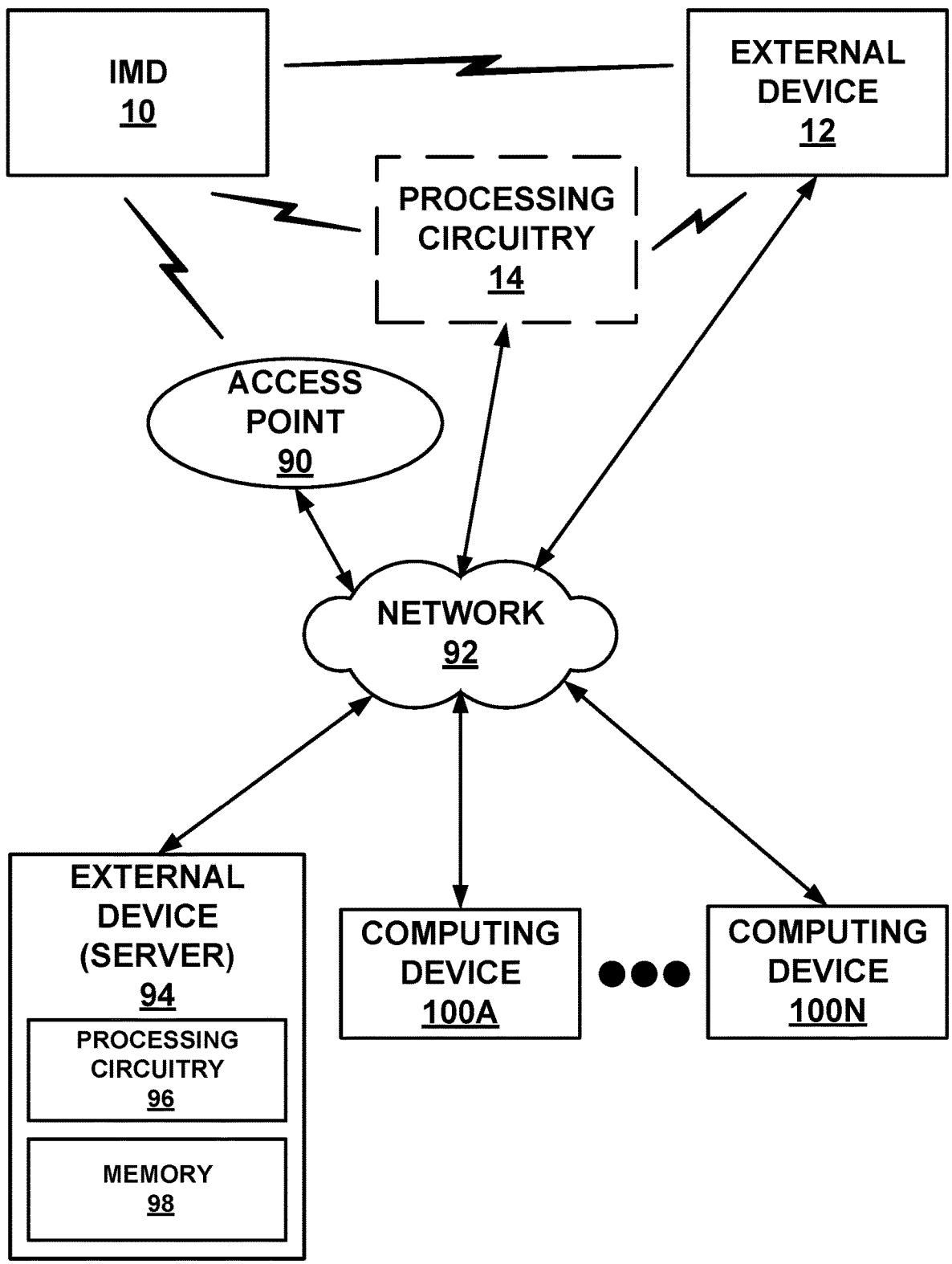
FIG. 6 is a block diagram illustrating an example system that includes an access point, a network, external computing devices, such as a server, and one or more other computing devices, which may be coupled to IMD, external device, and processing circuitry via network, in accordance with one or more techniques described herein.

FIG. 6 is a block diagram illustrating an example system that includes an access point 90, a network 92, external computing devices, such as a server 94, and one or more other computing devices 100A-100N, which may be coupled to IMD 10, external device 12, and processing circuitry 14 via network 92, in accordance with one or more techniques described herein. In this example, IMD 10 may use communication circuitry 54 to communicate with external device 12 via a first wireless connection, and to communication with an access point 90 via a second wireless connection. In the example of FIG. 6, access point 90, external device 12, server 94, and computing devices 100A-100N are interconnected and may communicate with each other through network 92.

Access point 90 may include a device that connects to network 92 via any of a variety of connections, such as telephone dial-up, digital subscriber line (DSL), or cable modem connections. In other examples, access point 90 may be coupled to network 92 through different forms of connections, including wired or wireless connections. In some examples, access point 90 may be a user device, such as a tablet or smartphone, that may be co-located with the patient. As discussed above, IMD 10 may be configured to transmit data, such as one or more sets of data to be analyzed in a fall risk analysis to external device 12. In addition, access point 90 may interrogate IMD 10, such as periodically or in response to a command from the patient or network 92, in order to retrieve parameter values determined by processing circuitry 50 of IMD 10, or other operational or patient data from IMD 10. Access point 90 may then communicate the retrieved data to server 94 via network 92.

In some cases, server 94 may be configured to provide a secure storage site for data that has been collected from IMD 10, and/or external device 12. In some cases, server 94 may assemble data in web pages or other documents for viewing by trained professionals, such as clinicians, via computing devices 100A-100N. One or more aspects of the illustrated system of FIG. 6 may be implemented with general network technology and functionality, which may be similar to that provided by the Medtronic CareLink® Network developed by Medtronic plc, of Dublin, Ireland.

Server 94 may include processing circuitry 96. Processing circuitry 96 may include fixed function circuitry and/or programmable processing circuitry. Processing circuitry 96 may include any one or more of a microprocessor, a controller, a DSP, an ASIC, an FPGA, or equivalent discrete or analog logic circuitry. In some examples, processing circuitry 96 may include multiple components, such as any combination of one or more microprocessors, one or more controllers, one or more DSPs, one or more ASICs, or one or more FPGAs, as well as other discrete or integrated logic circuitry. The functions attributed to processing circuitry 96 herein may be embodied as software, firmware, hardware or any combination thereof. In some examples, processing circuitry 96 may perform one or more techniques described herein based on one or more sets of data received from IMD 10, as examples.

Server 94 may include memory 98. Memory 98 includes computer-readable instructions that, when executed by processing circuitry 96, cause IMD 10 and processing circuitry 96 to perform various functions attributed to IMD 10 and processing circuitry 96 herein. Memory 98 may include any volatile, non-volatile, magnetic, optical, or electrical media, such as RAM, ROM, NVRAM, EEPROM, flash memory, or any other digital media.

In some examples, one or more of computing devices 100A-100N (e.g., device 100A) may be a tablet or other smart device located with a clinician, by which the clinician may program, receive alerts from, and/or interrogate IMD 10. For example, the clinician may access data corresponding to any one or more of an EGM, an impedance signal, a tissue perfusion signal, an accelerometer signal, and other types of signals collected by IMD 10 through device 100A, such as when patient 4 is in between clinician visits, to check on a status of a medical condition such as a fall risk score. In some examples, the clinician may enter instructions for a medical intervention for patient 4 into an app in device 100A, such as based on the fall risk score determined by IMD 10, external device 12, processing circuitry 14, or any combination thereof, or based on other patient data known to the clinician. Device 100A then may transmit the instructions for medical intervention to another of computing devices 100A-100N (e.g., device 100B) located with patient 4 or a caregiver of patient 4. For example, such instructions for medical intervention may include an instruction to change a drug dosage, timing, or selection, to schedule a visit with the clinician, or to seek medical attention. In further examples, device 100B may generate an alert to patient 4 based on a status of a the fall risk score of patient 4 determined by IMD 10, external device 12, processing circuitry 14, or any combination thereof, which may enable patient 4 proactively to seek medical attention prior to receiving instructions for a medical intervention. In this manner, patient 4 may be empowered to take action, as needed, to address his or her medical status, which may help improve clinical outcomes for patient 4.

Figure 7:
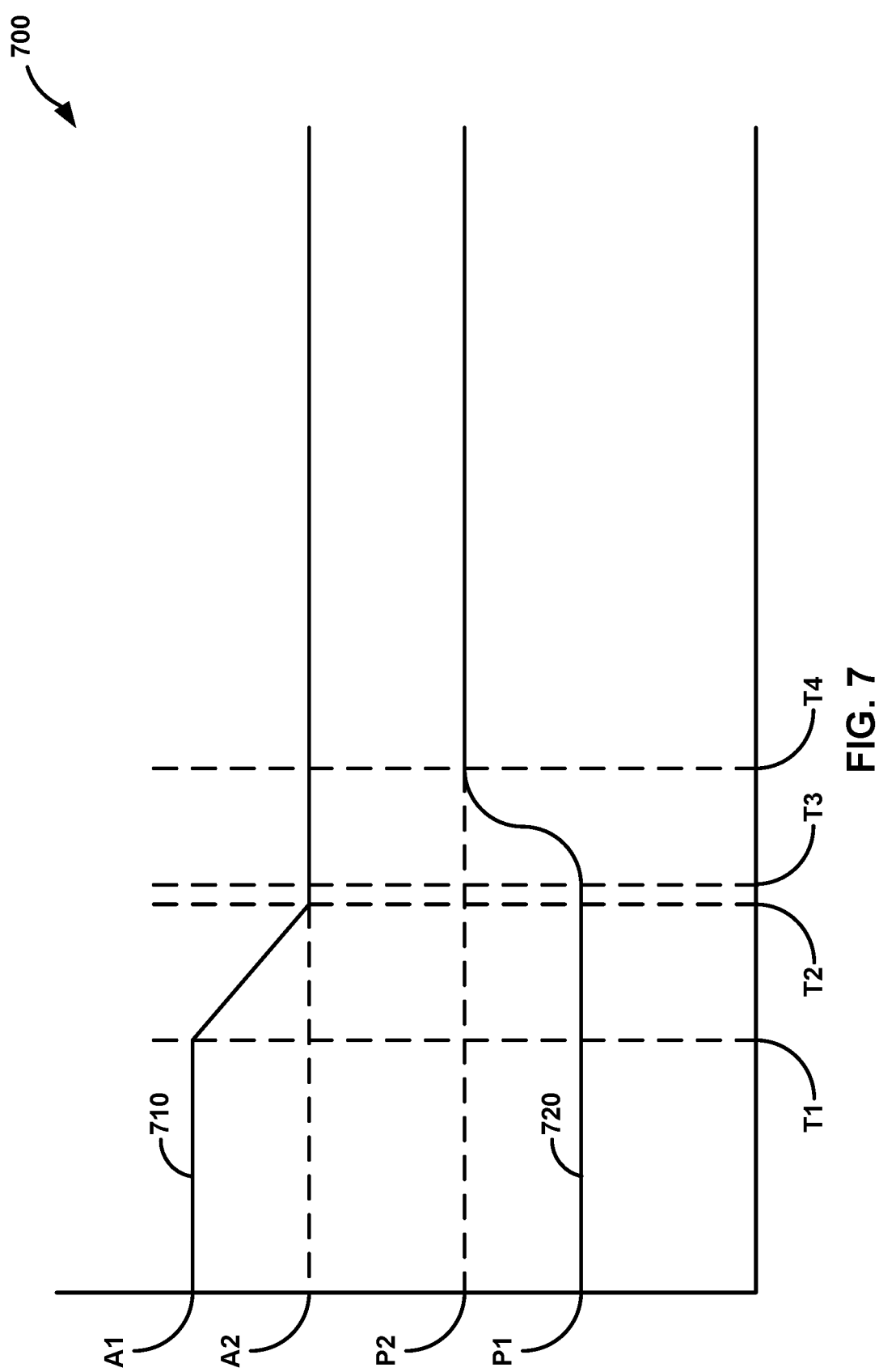
FIG. 7 is a graph illustrating an accelerometer signal plot and a physiological parameter plot, in accordance with one or more techniques described herein.

FIG. 7 is a graph illustrating an accelerometer signal plot 710 and a physiological parameter plot 720, in accordance with one or more techniques described herein. As seen in FIG. 7, the accelerometer signal plot 710 transitions from accelerometer signal value A1 to accelerometer signal value A2 over the period of time from time T1 to time T2. Subsequently, the physiological parameter plot 720 increases from parameter value P1 to parameter value P2 over the period of time from T3 to time T4.

The change in the accelerometer signal plot 710 from accelerometer signal value A1 to accelerometer signal value A2 may represent a body position movement or a body angle movement of patient 4. In some examples, the accelerometer signal plot 710 may represent a plot of one axis of a three-axis accelerometer signal generated by motion sensor(s) 42. In some examples, the accelerometer signal plot 710 may indicates a magnitude of a vector of two or more axes of the accelerometer signal generated by motion sensor(s) 42. In any case, the accelerometer signal plot 710 may be substantially constant at accelerometer signal value A1 prior to time T1 and the accelerometer signal plot 710 may be substantially constant at accelerometer signal value A2 following time T2, where the value A2 is lower than the value A1. Processing circuitry 14 may determine that the change in the accelerometer signal from A1 to A2 represents a body position change and processing circuitry 14 may generate a set of data including one or more signals indicative of the physiological parameter represented by physiological parameter plot 720.

In some cases, the physiological parameter plot 720 increases from parameter value P1 to parameter value P2 in response to the accelerometer signal plot 710 changing from accelerometer signal value A1 to accelerometer signal value A2. Since the change from accelerometer signal value A1 to accelerometer signal value A2 may represent a body position change of patient 4, the physiological parameter change from parameter value P1 to parameter value P2 may occur responsive to the body position movement detected by processing circuitry 14 in the accelerometer signal shown in accelerometer signal plot 710. In some examples, processing circuitry 14 may analyze the physiological parameter change from parameter value P1 to parameter value P2 in order to determine whether the physiological parameter change meets an expected parameter change. For example, the "expected" parameter change may represent a minimum change in the parameter value responsive to the body position change indicated by the accelerometer signal plot 710 change from accelerometer signal value A1 to accelerometer signal value A2. When the difference between P1 and P2 is greater than the expected parameter change, processing circuitry 14 may determine that the parameter change from P1 to P2 meets the expected parameter change. When the difference between P1 and P2 is not greater than the expected parameter change, processing circuitry 14 may determine that the parameter change from P1 to P2 does not meet the expected parameter change.

In some examples, physiological parameter plot 720 may indicate a parameter such as blood pressure, heart rate, tissue perfusion, motion data, or gyroscopic data. When the body position change indicated by the change from accelerometer signal value A1 to accelerometer signal value A2 is represents a sit-to-stand or a lying-to-stand body movement, it may be expected that some physiological parameters such as blood pressure and heart rate will increase in order to compensate for the increased exertion associated with these body position movements. Additionally, processing circuitry 14 may determine that a time in which it takes for patient 4 to complete a body position movement (e.g., the time from T1 to T2) changes across a sequence of body position movements of the same type. Processing circuitry 14 may determine the fall risk score associated with patient 4 based on the change in the amount of time that it takes to complete a body position movement. For example, patient 4 may complete a sequence of sit-to-stand movements. If the amount of time that it takes patient 4 increases from a beginning of the sequence to the end of the sequence of sit-to-stand movements, processing circuitry 14 may determine that the patient 4 is at an increased risk of falling.

Figure 8:
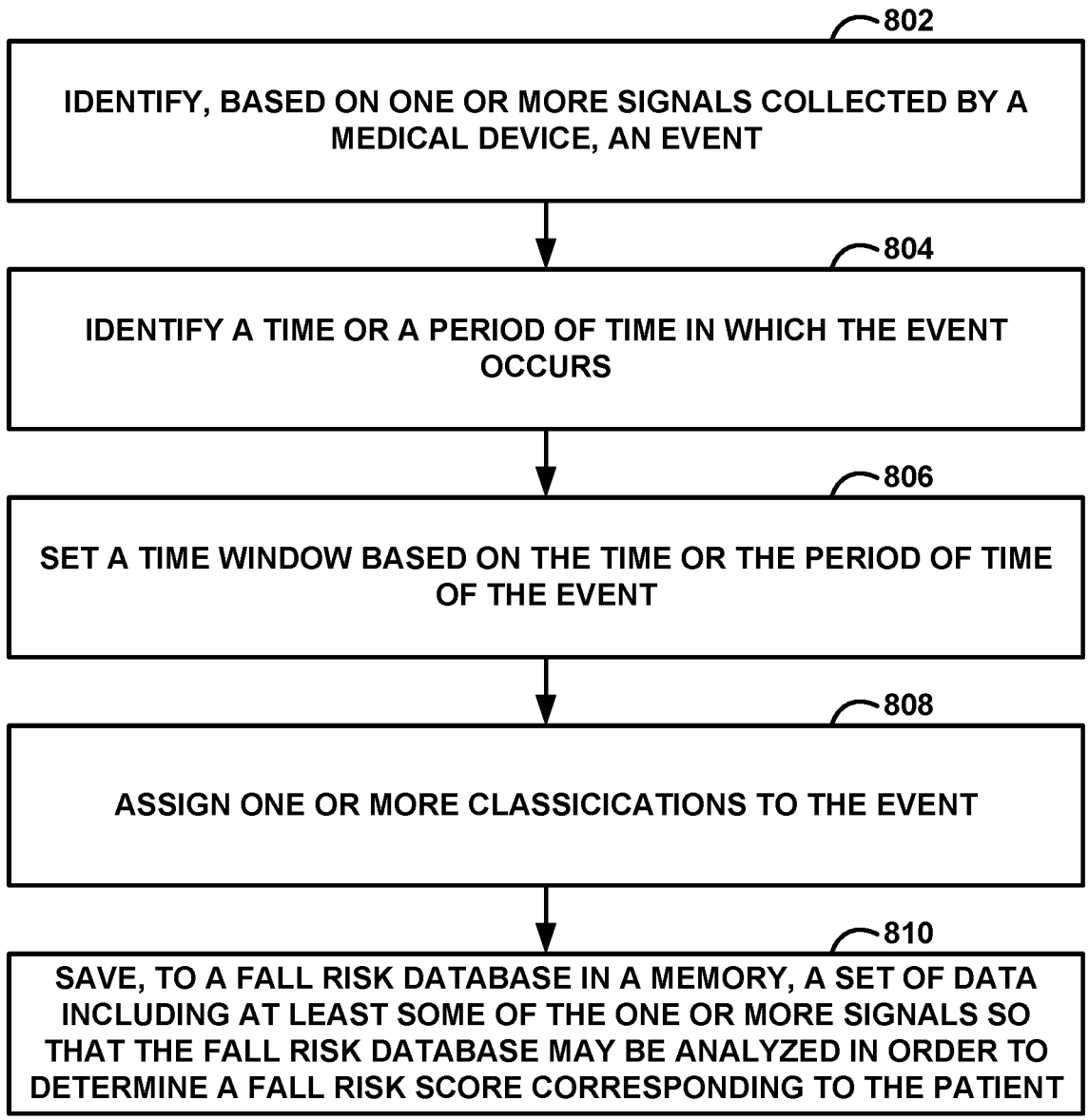
FIG. 8 is a flow diagram illustrating an example operation for generating data which may be analyzed to determine a fall risk score, in accordance with one or more techniques of this disclosure.

FIG. 8 is a flow diagram illustrating an example operation for generating data which may be analyzed to determine a fall risk score, in accordance with one or more techniques of this disclosure. FIG. 8 is described with respect to IMD 10, external device 12, and processing circuitry 14 of FIGS. 1-6. However, the techniques of FIG. 8 may be performed by different components of IMD 10, external device 12, and processing circuitry 14 or by additional or alternative medical device systems. Processing circuitry 14 is conceptually illustrated in FIG. 1 as separate from IMD 10 and external device 12 but may be processing circuitry of IMD 10 and/or processing circuitry of external device 12. In general, the techniques of this disclosure may be performed by processing circuitry 14 of one or more devices of a system, such as one or more devices that include sensors that provide signals, or processing circuitry of one or more devices that do not include sensors, but nevertheless analyze signals using the techniques described herein. For example, another external device (not pictured in FIG. 1) may include at least a portion of processing circuitry 14, the other external device configured for remote communication with IMD 10 and/or external device 12 via a network.

Processing circuitry 14 may identify one or more events based on data collected by IMD 10 and/or other medical devices or sensors. These events, when identified by processing circuitry 14, may represent reference points for analyzing data collected by the IMD 10 and/or other devices. For example, processing circuitry 14 may determine a time in which each identified event occurs and generate a set of data corresponding to each respective event. Additionally, processing circuitry 14 may classify each identified event according to one or more classifications and sort the set of data corresponding to each event into one or more bins associated with the one or more classifications assigned to the respective event. In turn, the processing circuitry 14 may analyze the sets of data in order to determine a fall risk score.

Processing circuitry 14 may identify, based on one or more signals collected by a medical device, an event (802). In some examples, the one or more signals include an accelerometer signal, an impedance signal (e.g., a subcutaneous impedance signal, an intrathoracic impedance signal, and/or an intracardiac impedance signal), and the event represents a body position movement event identified by processing circuitry 14 in the accelerometer signal. In some examples, the one or more signals include an EGM, an impedance signal (e.g., a subcutaneous impedance signal, an intrathoracic impedance signal, and/or an intracardiac impedance signal), a tissue oxygenation signal, or any combination thereof, and the event represents a cardiac event identified by processing circuitry 14 in the one or more signals. In some examples, the event represents another type of event identified in the accelerometer signal, the EGM, the impedance signal, the tissue oxygenation signal, another signal, or any combination thereof.

Processing circuitry 14 may identify a time or a period of time of the event (804). For example, when the event is a body position change, the processing circuitry 14 may determine, in the accelerometer signal, a time in which the body position change begins and a time in which the body position change ends. These times represent the period of time in which the body position change occurs. When the event is a cardiac event, the processing circuitry 14 may determine a time in which the cardiac event begins and a time in which the cardiac event ends. These times represent the period of time in which the cardiac event occurs.

Processing circuitry 14 may set a time window based on the time or period of time of the event (806). In some examples, the window of time may include at least a portion of time following the time or period of time in which the event occurs. In some examples, the entire window of time is after the time or period of time in which the event occurs. In some examples, at least a portion of the window of time occurs before the time or window of time in which the event occurs. Processing circuitry 14 may assign one or more classifications to the event (808). The one or more classifications may indicate aspects of the detected event. For example, the one or more classifications may include at least one type of body position movement, at least one type of body angle change, at least one time of day in which the event is detected, or at least one type of cardiac event.

Processing circuitry 14 may save, to a fall risk database in a memory, a set of data including at least some of the one or more signals so that the fall risk database may be analyzed in order to determine a fall risk score corresponding to patient 4 (810). For example, processing circuitry 14 may save a portion of one or more signals collected by IMD 10 or another medical device, where the portion of each respective signal corresponds to the window of time selected by processing circuitry 14. Processing circuitry 14 may save the set of data to one or more bins of the fall risk database based on the one or more classifications assigned to the event associated with the set of data. This allows processing circuitry 14 to analyze the one or more bins in order to determine a fall risk score associated with patient 4.

The techniques described in this disclosure may be implemented, at least in part, in hardware, software, firmware, or any combination thereof. For example, various aspects of the techniques may be implemented within one or more microprocessors, DSPs, ASICs, FPGAs, or any other equivalent integrated or discrete logic QRS circuitry, as well as any combinations of such components, embodied in external devices, such as physician or patient programmers, stimulators, or other devices. The terms "processor" and "processing circuitry" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as RAM, DRAM, SRAM, magnetic discs, optical discs, flash memories, or forms of EPROM or EEPROM. The instructions may be executed to support one or more aspects of the functionality described in this disclosure.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

What is claimed is:

1. A system comprising:
    an insertable cardiac monitor (ICM) comprising:
        a housing configured for subcutaneous implantation within a patient, the housing having a length, a width, and a depth,
            wherein the length is greater than the width and the width is greater than the depth, and
            wherein the length is within a range from 40 millimeters (mm) to 60 mm;
        an accelerometer to detect motion data indicative of activity level of the patient; and
        a plurality of electrodes positioned on the housing, wherein the ICM is configured to sense an electrocardiogram (ECG) of the patient via the plurality of electrodes;
    a remote computing device; and
    processing circuitry of at least one of the insertable cardiac monitor or the remote computing device, the processing circuitry configured to:
        periodically determine a respective value for each of a plurality of patient parameters based on the ECG and the activity level;
        output trends of the periodically determined values of the patient parameters at the remote computing device;
        determine a risk or occurrence of a cardiac event of the patient based on the trends of the periodically determined values of the patient parameters; and
        output an indication of the cardiac event based on the determination.

2. The system of claim 1, wherein the processing circuitry is further configured to:

determine activity level changes based on the detected motion data; and periodically determine the respective value for each of the plurality of patient parameters based on the ECG and the activity level changes.

3. The system of claim 2, wherein the processing circuitry is further configured to:
determine activity level changes during a particular time window; and
periodically determine the respective value for each of the plurality of patient parameters based on the ECG and the activity level changes during the particular time window.

4. The system of claim 2, wherein the processing circuitry is further configured to:
determine a pattern of the activity level changes; and
periodically determine the respective value for each of the plurality of patient parameters based on the ECG and the pattern of the activity level changes.

5. The system of claim 4, wherein the processing circuitry is further configured to:
determine a pattern of the activity level changes during a particular time window; and
periodically determine the respective value for each of the plurality of patient parameters based on the ECG and the pattern of the activity level changes during the particular time window.

6. The system of claim 1, wherein the motion data includes coordinate data.

7. The system of claim 1, wherein the accelerometer is a three-axis accelerometer configured to detect the motion data within a three-dimensional Cartesian space.

8. The system of claim 1, wherein the cardiac event is a heart failure event.

9. The system of claim 1, wherein the cardiac event is a fall event.

10. The system of claim 1, wherein the indication that is output comprises an indication of a risk of the cardiac event.

11. The system of claim 1, wherein the indication comprises one or more of an alert, recommendation for treatment, or a signal to cause one or more medical devices to deliver treatment.

12. The system of claim 1, wherein the processing circuitry is configured to determine a risk level of the cardiac event based on changes in the periodically determined values of the patient parameters over a time interval, and determine to present the indication of the cardiac event based the risk level.

13. A non-transitory computer-readable storage medium comprising program instructions that, when executed by processing circuitry, cause the processing circuitry to:
periodically determine a respective value for each of a plurality of patient parameters based on an electrocardiogram (ECG) and activity level of a patient detected by an insertable cardiac monitor (ICM), wherein the ICM comprises:
a housing configured for subcutaneous implantation within the patient, the housing having a length, a width, and a depth,
wherein the length is greater than the width and the width is greater than the depth, and
wherein the length is within a range from 40 millimeters (mm) to 60 mm;
an accelerometer to detect motion data indicative of the activity level of the patient; and
a plurality of electrodes, wherein the ICM is configured to sense the ECG via the plurality of electrodes;
output trends of the periodically determined values of the patient parameters at a remote computing device;
determine a risk or occurrence of a cardiac event of the patient based on the trends of the periodically determined values of the patient parameters; and
output an indication of the cardiac event based on the determination.

14. The non-transitory computer-readable storage medium of claim 13, wherein the program instructions that, when executed by processing circuitry, further cause the processing circuitry to
determine activity level changes based on the detected motion data; and
periodically determine the respective value for each of the plurality of patient parameters based on the ECG and the activity level changes.

15. The non-transitory computer-readable storage medium of claim 14, wherein the program instructions that, when executed by processing circuitry, further cause the processing circuitry to
determine activity level changes during a particular time window; and
periodically determine the respective value for each of the plurality of patient parameters based on the ECG and the activity level changes during the particular time window.

16. The non-transitory computer-readable storage medium of claim 14, wherein the program instructions that, when executed by processing circuitry, further cause the processing circuitry to
determine a pattern of the activity level changes; and
periodically determine the respective value for each of the plurality of patient parameters based on the ECG and the pattern of the activity level changes.

17. The non-transitory computer-readable storage medium of claim 16, wherein the program instructions that, when executed by processing circuitry, further cause the processing circuitry to:
determine a pattern of the activity level changes during a particular time window; and
periodically determine the respective value for each of the plurality of patient parameters based on the ECG and the pattern of the activity level changes during the particular time window.

18. The non-transitory computer-readable storage medium of claim 13 wherein the program instructions that, when executed by processing circuitry, further cause the processing circuitry to determine activity level of the patient based at least in part on the motion data.

19. The non-transitory computer-readable storage medium of claim 13, wherein the motion data includes coordinate data.

20. The non-transitory computer-readable storage medium of claim 13, wherein the accelerometer is a three-axis accelerometer configured to detect the motion data within a three-dimensional Cartesian space.

* * * * *